US011185611B2

(12) United States Patent
Gilbert et al.

(10) Patent No.: US 11,185,611 B2
(45) Date of Patent: Nov. 30, 2021

(54) METHOD AND APPARATUS FOR DECELLULARIZATION OF TISSUE

(71) Applicant: University of Pittsburgh—Of the Commonwealth System of Higher Education, Pittsburgh, PA (US)

(72) Inventors: Thomas W. Gilbert, Ellicott City, MD (US); Christopher M. Hobson, Pittsburgh, PA (US); Ethan N. Ungchusri, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 131 days.

(21) Appl. No.: 15/983,150

(22) Filed: May 18, 2018

(65) Prior Publication Data

US 2018/0264174 A1 Sep. 20, 2018

Related U.S. Application Data

(62) Division of application No. 15/123,471, filed as application No. PCT/US2015/018744 on Mar. 4, 2015, now Pat. No. 9,999,707.
(Continued)

(51) Int. Cl.
*A61L 27/36* (2006.01)
*C12M 1/42* (2006.01)
(Continued)

(52) U.S. Cl.
CPC ....... *A61L 27/3687* (2013.01); *A61L 27/3633* (2013.01); *A61L 27/3641* (2013.01); *A61L 27/3683* (2013.01); *A61L 27/3691* (2013.01); *C12M 1/40* (2013.01); *C12M 21/18* (2013.01); *C12M 35/04* (2013.01); *C12M 41/40* (2013.01); *C12M 45/02* (2013.01); *C12M 45/09* (2013.01); *G01N 1/31* (2013.01)

(58) Field of Classification Search
None
See application file for complete search history.

(56) References Cited

U.S. PATENT DOCUMENTS 3,892,197 A * 7/1975 Kinney .................. D06B 23/10
118/667
7,775,965 B2 8/2010 McFetridge
(Continued)

FOREIGN PATENT DOCUMENTS

EP 2138181 A1 12/2009
WO 9846165 A1 10/1998
(Continued)

OTHER PUBLICATIONS

Cole et al., Tracheal Basal Cells: A Facultative Progenitor Cell Pool, The American Journal of Pathology, 2010, vol. 177:1, pp. 362-376.
(Continued)

*Primary Examiner* — William H. Beisner
(74) *Attorney, Agent, or Firm* — The Webb Law Firm

(57) ABSTRACT

Methods of decellularization of tissue, such as mammalian tissue, are provided, along with methods of making an extracellular matrix (ECM) preparation. Systems and apparatus useful in performing the methods are also provided.

9 Claims, 17 Drawing Sheets

Related U.S. Application Data

(60) Provisional application No. 61/947,578, filed on Mar. 4, 2014.

(51) Int. Cl.
  C12M 1/40      (2006.01)
  G01N 1/31      (2006.01)
  C12M 1/33      (2006.01)
  C12M 1/00      (2006.01)
  C12M 1/34      (2006.01)

(56) References Cited

U.S. PATENT DOCUMENTS

| | | | |
|---|---|---|---|
| 2002/0115208 A1* | 8/2002 | Mitchell | C12N 5/0068 435/325 |
| 2005/0229323 A1* | 10/2005 | Mills | A61F 2/08 8/94.11 |
| 2008/0077251 A1* | 3/2008 | Chen | A61F 2/28 623/23.72 |
| 2012/0064050 A1 | 3/2012 | Calle et al. | |
| 2014/0023723 A1 | 1/2014 | Leach et al. | |
| 2016/0095956 A1 | 4/2016 | Ansari et al. | |
| 2017/0072100 A1 | 3/2017 | Gilbert et al. | |

FOREIGN PATENT DOCUMENTS

| | | | |
|---|---|---|---|
| WO | 2009025398 A1 | 2/2009 | |
| WO | 2010101962 A1 | 9/2010 | |
| WO | 2011022369 A2 | 2/2011 | |

OTHER PUBLICATIONS

Crapo et al., An overview of tissue and whole organ decellularization processes, Biomaterials, 2011, vol. 32:12, pp. 3233-3243.

Funamoto et al., The use of high-hydrostatic pressure treatment to decellularize blood vessels, Biomaterials, 2010, vol. 31:13, pp. 3590-3595.

Genden et al., Orthotopic tracheal transplantation in the murine model, Transplantation, 2002, vol. 73:9, pp. 1420-1425.

Genden et al., The Kinetics and Pattern of Tracheal Allograft Re-Epithelialization, Am J Respir Cell Mol Biol, 2003, vol. 28:6, pp. 673-681.

Genden et al., Orthotopic Tracheal Allografts Undergo Reepithelialization With Recipient-Derived Epithelium, Arch Otolaryngol Head Neck Surg, 2003, vol. 129:1, pp. 118-123.

Gilbert et al., Decellularization of tissues and organs, Biomaterials, 2006, vol. 27:19, pp. 3675-3683.

Gilbert, Strategies for Tissue and Organ Decellularization, Journal of Cellular Biochemisty, 2012, vol. 113:7, pp. 2217-2222.

Grillo, Tracheal Replacement: A Critical Review, Ann Thorac Surg, 2002, vol. 73:6, pp. 1995-2004.

Haykal et al., Evaluation of the Structural Integrity and Extracellular Matrix Components of Tracheal Allografts Following Cyclical Decellularization Techniques: Comparison of Three Protocols, Tissue Engineering: Part C, 2012, vol. 18:8, pp. 614-623.

Hua et al., Heterotopic and Orthotopic Tracheal Transplantation in Mice Used as Models to Study the Development of Obliterative Airway Disease, Journal of Visualized Experiments, 2010, vol. 35, pp. 1-4.

Kocyildirim et al., Long-segment tracheal stenosis: slide tracheoplasty and a multidisciplinary approach improve outcomes and reduce costs, The Journal of Thoracic and Cardiovascular Surgery, 2004, vol. 128:6, pp. 876-882.

Kutten et al., Decellularized Tracheal Extracellular Matrix Supports Epithelial Migration, Differentiation, and Function, Tissue Engineering: Part A, 2015, vol. 21:1-2, pp. 75-84.

Musah et al., Repair of tracheal epithelium by basal cells after chlorine-induced injury, Respiratory Research, 2012, vol. 13:107, pp. 1-12.

Negishi et al., Porcine radial artery decellularization by high hydrostatic pressure, Journal of Tissue Engineering and Regenerative Medicine, 2015, vol. 9:11, pp. E144-E151.

Okumura et al.. Experimental study on a new tracheal prosthesis made from collagen-conjugated mesh, The Journal of Thoracic and Cardiovascular Surgery, 1994, vol. 108:2, pp. 337-345.

Shafiq et al., Decellularized Human Cornea for Reconstructing the Corneal Epithelium and Anterior Stroma, Tissue Engineering: Part C, 2012, vol. 18:5, pp. 340-348.

Teramachi et al., Intrathoracic tracheal reconstruction with a collagen-conjugated prosthesis: evaluation of the efficacy of omental wrapping, The Journal of Thoracic and Cardiovascular Surgery, 1997, vol. 113:4, pp. 701-711.

Wurtz et al., Tissue-Engineered Airway in the Clinical Setting: A Call for Information Disclosure, Clinical Pharmacology & Therapeutics, 2012, vol. 91:6, p. 973.

Eichhorn et al., Pressure Shift Freezing as Potential Alternative for Generation of Decellularized Scaffolds, International Journal of Biomaterials, 2013, vol. 2013, pp. 1-7.

Montoya et al., Preparation of Ex Vivo-Based Biomaterials Using Convective Flow Decellularization, Tissue Engineering, Part C: Methods, 2009, vol. 15, pp. 191-200.

Struecker et al., Improved Rat Liver Decellularization by Arterial Perfusion Under Oscillating Surrounding Pressure, International Journal Artificial Organs, 2013, vol. 36(8), p. 585.

* cited by examiner

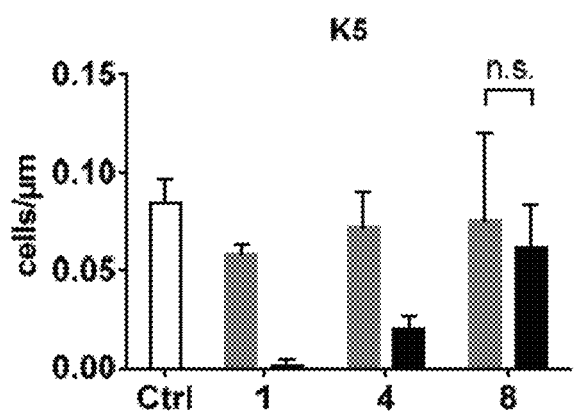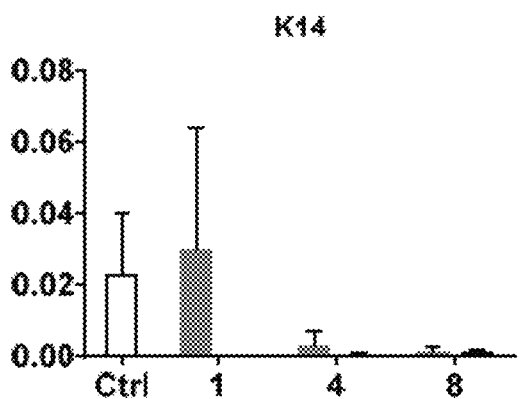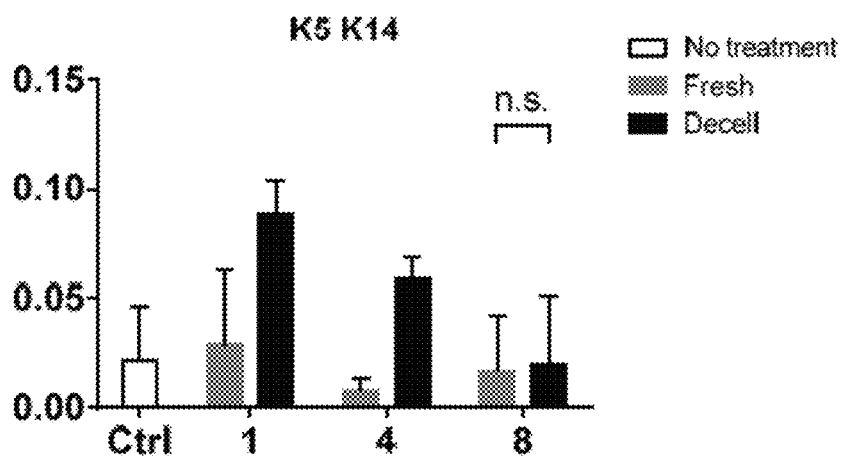
Fig. 2-3

METHOD AND APPARATUS FOR DECELLULARIZATION OF TISSUE

CROSS REFERENCE TO RELATED APPLICATIONS

This application is a divisional of U.S. patent application Ser. No. 15/123,471 filed Sep. 2, 2016, which is a national stage of International Patent Application No. PCT/US2015/018744, filed Mar. 4, 2015, which claims the benefit of U.S. Provisional Patent Application No. 61/947,578, filed Mar. 4, 2014, each of which is incorporated herein by reference in its entirety.

BACKGROUND

Methods of decellularization of tissue, such as mammalian tissue, are provided, along with methods of making an extracellular matrix (ECM) preparation. Systems and apparatus useful in performing the methods are also provided.

ECM materials have found broad use in the field of regenerative medicine. A variety of methodologies for the preparation of ECM materials exist, occasionally meeting with success, as evidenced by the many commercial products available. However, there are limitations to the methods, such as ECM materials with inferior mechanics, such as failure stress and stiffness as compared to the mechanical qualities actually needed in many instances. Further, traditional methods do not necessarily work on certain tissue types and can be overly destructive to the ECM structure, resulting in ECM material that is useless or sub-optimal for a desired end use.

Tracheal defects or stenosis can result from congenital defects, trauma, or various pathologies such as cancer or infection. Partial loss of airway in a patient is debilitating and life-threatening. In pediatric patients surgical approaches including, slide tracheoplasty has been employed successfully. In adults trachea mobilization has enabled post-resection repair in some cases. Long-term stenting, dilation, and tracheostomy have been employed as palliative care in some patients. However, regardless of the approach complication rates remains very high and long term morbidity is common. There remains a cohort of patients for which standard approaches cannot be employed. Therefore, a functional tracheal replacement graft is still desirable.

Initially, engineered tracheal grafts were consisted of purified collagen sponges around a stent or synthetic scaffold (Okumura, N., et al., Experimental study on a new tracheal prosthesis made from collagen-conjugated mesh. *J Thorac Cardiovasc Surg*, 1994. 108(2): p. 337-45 and Teramachi, M., et al., Intrathoracic tracheal reconstruction with a collagen-conjugated prosthesis: evaluation of the efficacy of omental wrapping. *J Thorac Cardiovasc Surg*, 1997. 113(4): p. 701-11). Though widely used, these have had multiple deficiencies. Failure of the first engineered tracheas resulted from several causes including infection, stenosis, and complete disintegration (Wurtz, A. and E. Kipnis, Tissue-engineered airway in the clinical setting: a call for information disclosure. Clin Pharmacol Ther, 2012. 91(6): p. 973; author reply 974). Current engineered tracheas are considerably more complex and employ both multiple graft modifications and recipient treatments. Common to all is a foundation built upon a decellularized tracheal allograft or a synthetic nanofiber scaffold to provide structural support. These scaffolds are then seeded with mature airway cells or stem cells and transplanted to recipients pre-treated with growth factors (Gilbert, T. W., et al., Decellularization of tissues and organs. *Biomaterials*, 2006. 27(19): p. 3675-83 and Gilbert, T. W., Strategies for tissue and organ decellularization. *J Cell Biochem*, 2012. 113(7): p. 2217-22). Finally pedicalled island flaps are wrapped around the engineered tracheal transplant to provide a vascular source (Teramachi, M., et al., Intrathoracic tracheal reconstruction with a collagen-conjugated prosthesis: evaluation of the efficacy of omental wrapping. *J Thorac Cardiovasc Surg*, 1997. 113(4): p. 701-11). Considering the extreme and urgent conditions under which these engineered tracheas were transplanted, the strategy has shown modest success, arguably more so with the decellularized allografts than with the synthetic scaffolds based upon mortality rates to date. Further, despite the publication of clinical transplantation reports of the current generation of engineered tracheas, the molecular and cellular processes controlling the survival of the engineered tracheal grafts remain incompletely defined. There is a need for superior decellularized ECM material, for example, decellularized trachea materials.

SUMMARY

Provided herein are methods of making decellularized ECM material. The material is decellularized by application of a pressure differential to the tissue to be decellularized, such as a cyclical pressure differential, resulting in an ECM material that is superior in many instances to ECM materials decellularized by other methods, such as by use of boiling water, agitation, or acids, which can damage the end-product. According to certain embodiments, the tissue is placed in a hypertonic or a hypotonic solution that optionally contains one or more of a detergent; an enzyme; and/or an acid, such as peracetic acid. Also provided is a system or apparatus comprising a vacuum chamber including a tissue cassette, optionally comprising a tissue sample to be decellularized.

A method of decellularizing tissue is provided. The method comprises changing a pressure at least one time to decellularize the tissue sample. The pressure is changed by any useful method, such as by changing pressure within an airtight chamber. Thus, according to one embodiment, the tissue sample is placed into an airtight chamber and pressure is changed in the container. An airtight container may be any size, ranging, for example and without limitation, from a small bench-top vacuum chamber, such as the chamber shown in connection with the examples below, to a room-sized container, e.g., a room, facilitating bulk decellularization of large quantities of tissue. In one embodiment, the tissue sample is immersed in a decellularization solution and is optionally agitated during application of the pressure change. Non-limiting examples of a decellularization solution is an aqueous solution such as water, phosphate-buffered saline (PBS) or saline. According to further embodiments, the solution further comprises one or more of a surfactant, a salt, a sugar, an acid, a protease, or a DNAse, for example and without limitation the decellularization solution is an aqueous solution comprising one or more of: SDS; CHAPS; deoxycholate; Triton X-100; Trypsin; DNAse; Proteinase K; NaCl; glucose; urea; or peracetic acid. In one embodiment, the decellularization solution comprises Triton X-100 and NaCl. According to one embodiment, the method further comprises after changing the pressure in the chamber at least one time, agitating the tissue in a solution comprising peracetic acid and ethanol. In one embodiment, the pressure is changed cyclically with a frequency of from 5 seconds to one hour, for example the pressure is changed cyclically with a frequency of from 5 seconds to 30 minutes and in one embodiment from 1 to 2 minutes. The duty cycle, a ratio of the time it takes to pressurize or evacuate to how long a pressure is held, ranges in one embodiment from 15% to 90%. In one embodiment, relative pressure ramp rates, that is the rate of pressure change during pressurization or evacuation, ranges from 0.25 MPa/s to 0.0001 MPa/s. In one embodiment, the pressure is changed at least about 10% or at least about 25%. For example a change of pressure from 1 atm to 2 atm is a 200% change, a change from 2 atm to 0.5 atm is a 75% change, a change of from 2 atm to 1 atm is a 50% change, and a change of from 0.5 atm to 2 atm is a 400% change. The pressures may range above or below ambient, environmental pressure, such as above or below 1 atm or 0.1013 MPa. In another embodiment, the pressure is changed at least about 0.10 MPa, or at least about 0.25 MPa. A typical absolute pressure range is from 0.93 MPa to 0.006 MPa, and values and increments therebetween.

Also provided is a method of preparing an ECM material, comprising decellularizing tissue according to any method described herein, and sterilizing, packaging and/or drying, cryopreserving, freezing or lyophilizing the decellularized tissue. In one embodiment, the method comprises decellularizing the tissue and sterilizing, packaging and drying, cryopreserving, freezing or lyophilizing the decellularized tissue.

Also provided is a system for decellularization of tissue, comprising: an airtight chamber; a pump connected to the airtight chamber; one or more valves for controlling air flow into and from the airtight chamber; and a computer control comprising one or more processes for changing pressure at least one time in the airtight chamber. In one embodiment, the airtight chamber comprises a tissue sample in a decellularization solution. In another embodiment, processes cyclically control pressure change in the airtight chamber with a cycle length of from 15 seconds to one hour, a pressure change of at least 25%, and at least 10 pressure changes.

In further embodiments, methods of preparing tissue, such as trachea tissue, are provided. The tissue is prepared by implanting the decellularized tissue prepared according to any method described herein, in a patient. This can be used for trachea repair, by orthotopically implanting decellularized trachea as described herein in a patient's airway.

BRIEF DESCRIPTION OF THE DRAWINGS

(FIG. 1A) Still frames from video recording of tracheal transplant performed in a wild-type mouse. Survival (FIG. 1B, fresh: n=7, decellularized: n=17) and weight gain (FIG. 1C, n>3 at each time point) over four weeks following surgery shown.

FIGS. 3-1 through 3-3. Histologic quantification of ciliated and secretory cell maturation in mouse trachea transplants. Mice receiving fresh (a, b, e, f, i, j) or decellularized (c, d, g, h, k, l) transplants were sacrificed one (a-d), four (e-i), or eight (i-l) weeks following surgery and immunofluorescent labeling for markers of mature epithelial cells was performed. Images are shown at a site of anastomosis (a, e, i, c, g, k) or at a mid-graft location (b, f, j, d, h l). Cells expressing acetylated tubulin (ACT, red, m) and Clara cell secretory protein (CCSP, green, n) along the basement membrane were counted in order to determine cell densities (cells/μm). Columns labeled "Ctrl" denote cell densities for untreated, native trachea from C57BL/6 mice. Scale bar 200 μm.

DESCRIPTION OF THE INVENTION

Figure 1A:
FIGS. 1A-1C. Orthotopic transplantation or fresh tracheal grafts is associated with superior recovery post operatively. Orthotopic transplants of fresh and decellularized tracheal grafts were performed on wild-type C57BL/6 mice.
Figure 1A:
Figure 1A:
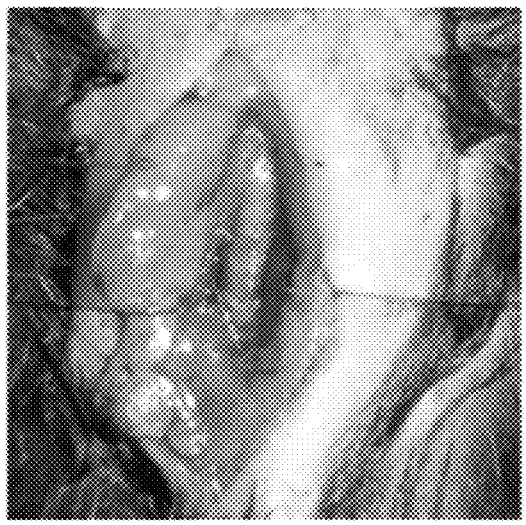
Figure 1A:
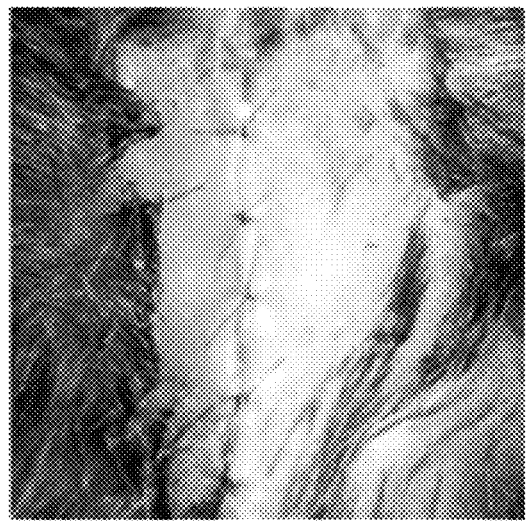

Provided herein is a superior method for decellularizing tissue for use in regenerative medicine.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the terms "extracellular matrix" and "ECM" refer to a natural scaffolding for cell growth. ECM, found in multicellular organisms, such as mammals and humans, are complex mixtures of structural and non-structural biomolecules, including, but not limited to, collagens, elastins, laminins, glycosaminoglycans, proteoglycans, antimicrobials, chemoattractants, cytokines, and growth factors. In mammals, ECM often comprises about 90% collagen, in its various forms. The composition and structure of ECMs vary depending on the source of the tissue. For example, brain, trachea, vascular, cardiac, small intestine submucosa (SIS), urinary bladder matrix (UBM), liver stroma ECM, and dermal ECM each differ in their overall structure and composition due to the unique cellular niche needed for each tissue.

By "biocompatible", it is meant that a device, scaffold composition, etc. is essentially, practically (for its intended use) and/or substantially non-toxic, non-injurious or non-inhibiting or non-inhibitory to cells, tissues, organs, and/or organ systems that would come into contact with the device, scaffold, composition, etc.

In general, the method of preparing an ECM material requires the isolation of ECM from an animal of interest and from a tissue or organ of interest. In certain embodiments, the ECM is isolated from mammalian tissue. As used herein, the term "mammalian tissue" refers to tissue derived from a mammal, wherein tissue comprises any cellular component of an animal. For example and without limitation, tissue can be derived from aggregates of cells, an organ, portions of an organ, or combinations of organs. In certain embodiments, the ECM is isolated from a vertebrate animal, for example and without limitation, human, monkey, pig, cattle, and sheep. In certain embodiments, the ECM is isolated from any adult, neonatal or fetal tissue of an animal, for example and without limitation, airway, trachea, vocal fold, lung, urinary bladder, liver, intestine, esophagus, pancreas, dermis, myocardium, heart valve, thoracic aorta, abdominal aorta, ocular such as retina, CNS such as brain or spinal cord, peripheral vasculature, peripheral nerves, skeletal muscle and orthopedic sources such as nucleus polopsus, cartilage (e.g., knee and temporomandibular joint), tendon and bone.

As an example, and where applicable, the ECM is derived from tissue that includes all portions/components of the tissue from which it is derived, or less than all portions/components of that tissue source. For example, where applicable, the ECM may or may not include the basement membrane portion of the ECM. In certain embodiments, the ECM includes at least a portion of the basement membrane. The ECM may or may not retain some of the cellular elements that comprised the original tissue such as capillary endothelial cells or fibrocytes.

As used herein, the term "derive" and any other word forms of cognates thereof, such as, without limitation, "derived" and "derives", refers to a component or components obtained from any stated source by any useful method. For example and without limitation, an ECM-derived material refers to a material comprised of components of ECM obtained from any tissue by any number of methods known in the art for isolating ECM, for example as described herein. In another example, mammalian tissue-derived ECM refers to ECM comprised of components of a particular mammalian tissue obtained from a mammal by any useful method.

Tissue for preparation of ECM materials can be harvested in a large variety of ways and once harvested, a variety of portions of the harvested tissue may be used. For example and without limitation, in one embodiment, the ECM is isolated from harvested porcine urinary bladder to prepare urinary bladder matrix (UBM). Excess connective tissue and residual urine are removed from the urinary bladder. The tunica serosa, tunica muscularis externa, tunica submucosa and most of the muscularis mucosa is removed in one embodiment, by mechanical abrasion or by a combination of enzymatic treatment, hydration, and abrasion. Mechanical removal of these tissues can be accomplished by abrasion using a longitudinal wiping motion to remove the outer layers (particularly the abluminal smooth muscle layers) and even the luminal portions of the tunica mucosa (epithelial layers). Mechanical removal of these tissues is accomplished by removal of mesenteric tissues with, for example, Adson-Brown forceps and Metzenbaum scissors and wiping away the tunica muscularis and tunica submucosa using a longitudinal wiping motion with a scalpel handle or other rigid object wrapped in moistened gauze.

In one embodiment, the ECM is prepared by abrading porcine bladder tissue to remove the outer layers including both the tunica serosa and the tunica muscularis using a longitudinal wiping motion with a scalpel handle and moistened gauze. Following eversion of the tissue segment, the luminal portion of the tunica mucosa is delaminated from the underlying tissue using the same wiping motion. Care is taken to prevent perforation of the submucosa. After these tissues are removed, the resulting ECM consists mainly of the tunica submucosa.

In another embodiment, dermal tissue is used as the source of ECM. Dermal tissue may be obtained from any mammalian source, such as human, monkey, pig, cow and sheep. In one embodiment, the source is porcine. Porcine skin from the dorsolateral flank of market weight pigs immediately can be harvested and processed as described herein, and can be delaminated to remove subcutaneous fat, connective tissue and the epidermis. The harvested sheets of porcine dermis can be immediately frozen at $-80°$ C. for storage.

In another embodiment, the epithelial cells are delaminated first by first soaking the tissue in a de-epithelializing solution such as hypertonic saline, for example and without limitation, 1.0 N saline, for periods of time ranging from 10 minutes to 4 hours. Exposure to hypertonic saline solution effectively removes the epithelial cells from the underlying basement membrane. The tissue remaining after the initial delamination procedure includes epithelial basement membrane and the tissue layers abluminal to the epithelial basement membrane. This tissue is next subjected to further treatment to remove the majority of abluminal tissues but not the epithelial basement membrane. The outer serosal, adventitial, smooth muscle tissues, tunica submucosa and most of the muscularis mucosa are removed from the remaining de-epithelialized tissue by mechanical abrasion or by a combination of enzymatic treatment, hydration, and abrasion.

Figure 7:
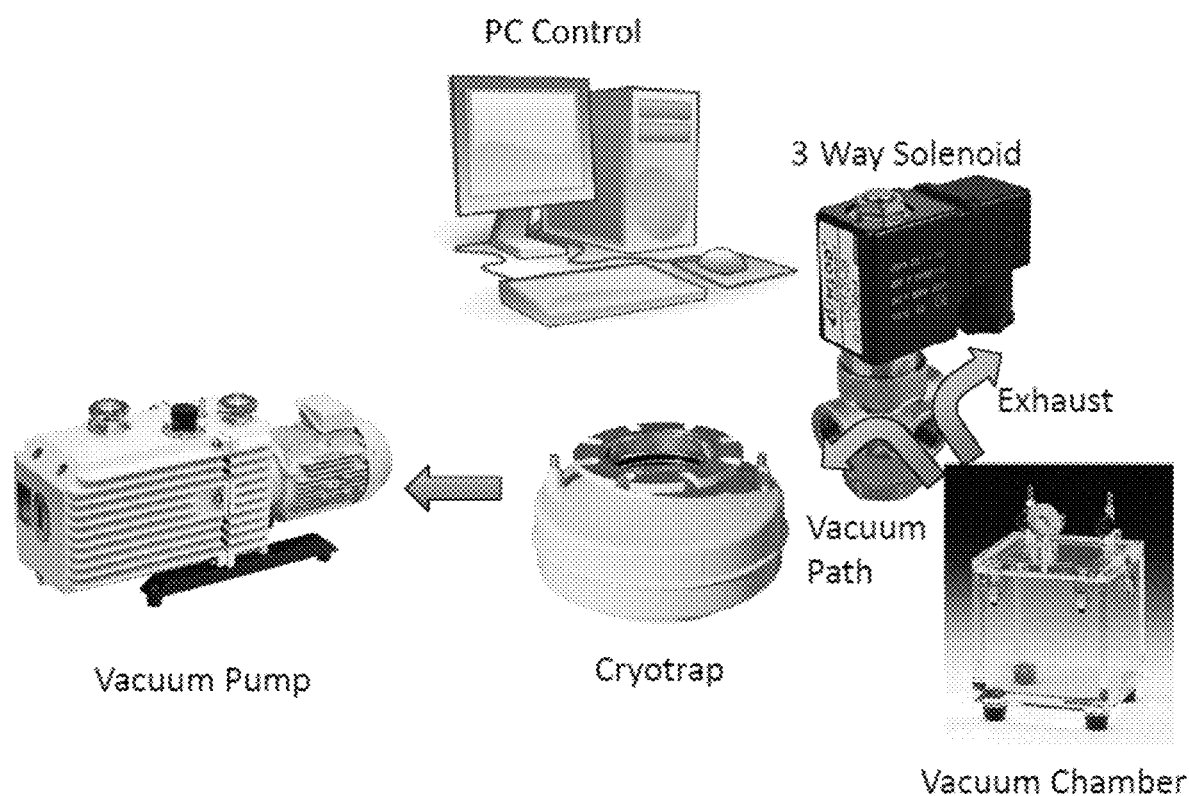
FIG. 7 is a diagram of components of one embodiment of a vacuum system as described herein.

Methods described herein utilize pressure changes to enhance the decellularization process for tissue. The pressure change can be applied by any of a variety of methods. According to one non-limiting embodiment depicted in FIG. 7, a vacuum chamber is connected to a solenoid, a cryotrap and a vacuum pump via a solenoid or any other suitable valve configuration. The vacuum pump is used to change pressure in the vacuum chamber and the solenoid is electronically controlled by a PC (personal computer), or any other applicable computing device, such as a tablet or smartphone. A vacuum or pressure can be applied by any of a multitude of possible configurations either understood or readily envisionable by those of ordinary skill.

The pressure difference may be applied once or more than once at irregular or regular time periods. The timing for applying one or more pressure changes is infinitely variable, though variations of exceptionally long periods may prove impracticable for commercial or other reasons. According to one example, the pressure change is applied cyclically or regularly with a cycle period ranging from seconds, to minutes, to hours. In one embodiment, the number of cycles is at least one. A cycle, or cycling, means a change of pressure in one direction (increase or decrease) from an original pressure followed by a change of pressure in the opposite direction, for example and without limitation, returning to the original pressure. As an example, a vacuum (evacuation) is applied, followed by a pressurization; for example first decreasing pressure from an original value and subsequently increasing the pressure to the original value or substantially to the original value. In another example, pressure is applied followed by evacuation; for example, first increasing pressure from an original value and subsequently returning the pressure to the original value by evacuation. In another embodiment, the change in pressure in a cycle is from a first value to a second value, higher or lower than the first value, and a return from the second value to the first value, or a change in pressure from the second value towards (in the direction of) the first value. In one embodiment, the pressure in a cycle is raised or lowered from a first value to a second value and then returned to the first value. For example, the cycle period may be 5, 10, 15, 20, 25, 30, 45 or 60 seconds, 2, 3, 4, 5, 10, 15, 20, 30, 45 or 60 minutes, or 2, 3, 4, 5, 6, 9 or 12 hours or any increment therebetween. In one embodiment, the cycle time ranges from 5 seconds to 30 minutes, in another, it ranges from 1 to 2 minutes, with the vacuum chamber being evacuated between 50% and 90% of the time. In one embodiment, relative pressure ramp rates, that is the rate of pressure change during pressurization or evacuation, ranges from 0.25 MPa/s to 0.0001 MPa/s. The duty cycle of the pressure/vacuum system is a percentage of time the system is held at a fixed pressure. A non-limiting example of a duty cycle is 15% to 90% of cycle time at a fixed pressure. The pressure may also be changed irregularly with the same exemplary time limits. Although the pressure may be changed once, more typically the pressure is changed two or more and at least 5, 10, 15, 20, 25, or 50 times, including increments therebetween. The pressure change may be small, such as a difference of 1-5%, larger, such as a difference of 10-25%, or even larger ranging above 25% or 50%. An example differential may be between atmospheric pressure (1 atmosphere or ~0.101 MPa (megapascal)) and any fraction or multiple thereof, such as 0.001 or lower, 0.01, 0.02, 0.03, 0.04, 0.05, 0.06, 0.07, 0.08, 0.09, 0.095, 0.1, 0.125, 0.15, 0.25, 0.5 or 1 MPa. The pressure change may be between values above, and/or values below 1 atmosphere, so long as there is a pressure change. For example, in one embodiment, both the maximum and minimum pressure are less than one atmosphere. In another, both the maximum and minimum pressure are above one atmosphere (positive pressure). In yet another embodiment, the minimum is below one atmosphere and the maximum is above one atmosphere. As a non-limiting example, the particular system depicted in FIG. 7 and described in the examples below has a useful range of from −0.095 MPa to 0.415 MPa. A maximum pressure change and/or maximizing the vacuum is preferred in embodiments. As would be understood by those of ordinary skill, the values, such as, without limitation, the cycle time, pressure ramp rates, starting and ending pressures in a cycle, duty cycle, pressure hold times, and pressure change can be varied over the course of the decellularization process.

During decellurization and during the application of a pressure change, the tissue to be decellularized is placed in a hypotonic, a hypertonic or an isotonic decellularization solution and is optionally agitate, e.g., on a shaker. The solution may be water, such as distilled, filtered or deionized water, PBS (phosphate-buffered saline), or saline. Surfactants, ionic or non-ionic, such as, without limitation, SDS (sodium dodecyl sulfate), CHAPS (e.g., 3-[(3-Cholamidopropyl)dimethylammonio]-1-propanesulfonate), deoxycholate or Triton X-100 (e.g., 4-(1,1,3,3-Tetramethylbutyl) phenyl-polyethylene glycol) optionally are included in the solution. Enzymes, such as, without limitation, Trypsin, DNAse or Proteinase K also optionally are included in the solution. Salts and sugars, such as, without limitation, NaCl, glucose, or urea optionally are included in the solution. An acid, such as peracetic acid ($CH_3CO_3H$) also may be included in the solution.

Decellularized ECM can then be dried, either lyophilized (freeze-dried) or air dried. The material is optionally sterilized, e.g., by gamma radiation or ethylene oxide exposure. The ECM is optionally comminuted. Dried ECM can be comminuted by methods including, but not limited to, tearing, milling, cutting, grinding, and shearing. The comminuted ECM can also be further processed into a powdered form by methods, for example and without limitation, such as grinding or milling in a frozen or freeze-dried state. As used herein, the term "comminute" and any other word forms or cognates thereof, such as, without limitation, "comminution" and "comminuting", refers to the process of reducing larger particles into smaller particles, including, without limitation, by grinding, blending, shredding, slicing, milling, cutting, shredding. ECM can be comminuted while in any form, including, but not limited to, hydrated forms, frozen, air-dried, lyophilized, powdered, sheet-form. In yet another embodiment, the ECM material, e.g., comminuted, is digested with a protease, and can be used for serum supplementation or in cell culture.

In one embodiment, the ECM is prepared from trachea tissue, for example and without limitation as described below. In use, the decellularized ECM may be affixed in place in the trachea, e.g., anamastosed by any useful manner, including without limitation, suturing or stapling. Alternately, anamastosis of ends of a trachea may be reinforced by overlaying the trachea-derived ECM material over the anamastosis site.

In one embodiment, a method of preparing an ECM material in provided, comprising decellularizing tissue with a pressure-change step, according to any method described herein, and sterilizing, packaging (e.g., in suitable vessels, containers, foil and/or polymeric pouches, etc. according to acceptable packaging practices for implantable medical devices) and/or drying, cryopreserving, freezing or lyophilizing the decellularized tissue. In one embodiment, the method comprises decellularizing the tissue, sterilizing, and drying, cryopreserving, freezing or lyophilizing the decellularized tissue.

As described above, a system is provided for decellularization of tissue, comprising: an airtight chamber; a pump connected to the airtight chamber; one or more valves for controlling air flow into and from the airtight chamber; and a computer control comprising one or more processes for changing pressure at least one time in the airtight chamber. The airtight chamber is any suitable chamber, vessel, container, room, etc. capable of withstanding the varying pressures used to prepare the tissue, which can be negative and/or positive pressures in relation to atmospheric pressure. In one embodiment, the airtight chamber comprises a tissue sample in a decellularization solution. In another embodiment, processes cyclically control pressure change in the airtight chamber with a cycle length of from 15 seconds to one hour, a pressure change of at least 25%, and at least 10 pressure changes. Any variation on pressure change parameters as described herein may be implemented by the processes.

One of ordinary skill can devise and implement a suitable process for implementing the computational framework by which pressure changes, such as cyclical pressure changes in an airtight chamber may be implemented using, e.g., a common pressure/vacuum pump and one or more valves, such as one or more solenoids.

Figure 10:
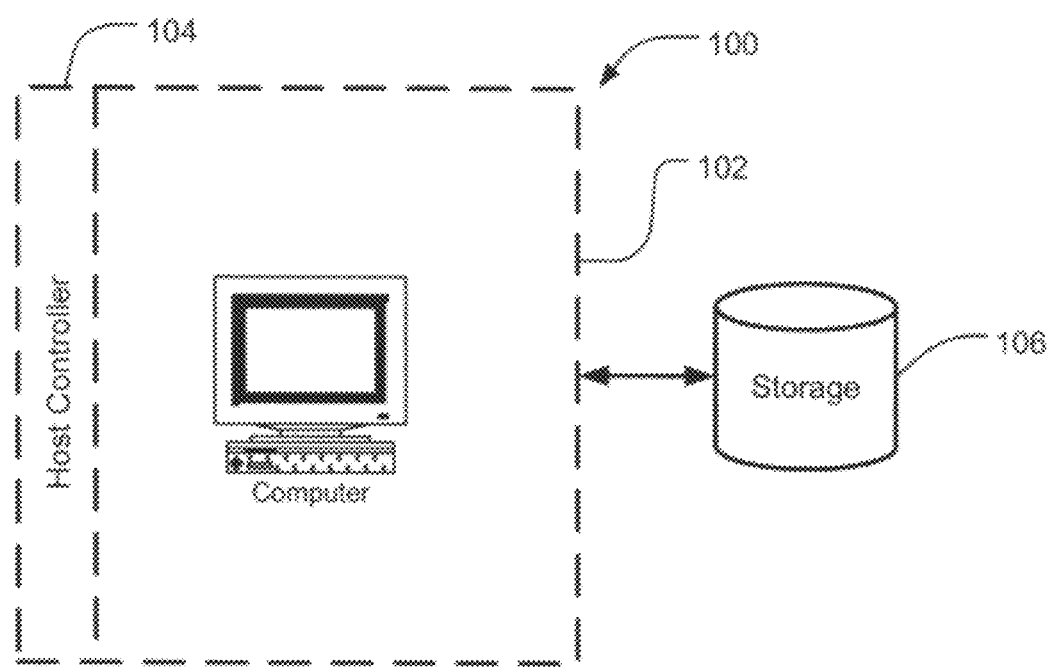
FIG. 10 is a schematic depiction of a computer.

Processes are implemented on an electronic computing device (computer), e.g., by a microprocessor. In the context of computing, a process is, broadly speaking any computer-implemented activity that generates an outcome, such as implementation of a mathematical or logical formula or operation, algorithm, etc. FIG. 10 illustrates one embodiment of a system 100 for implementing a modeling system. The system 100 may include a device 102 operating under the command of a controller 104. Device 102 may be referred to herein, without limitation, as a computer or computing device. The broken lines are intended to indicate that in some implementations, the controller 104, or portions thereof considered collectively, may instruct one or more elements of the device 102 to operate as described. Accordingly, the functions associated with the processes (e.g., software, programs) described herein may be implemented as software executing in the system 100 and controlling one or more elements thereof. An example of a device 102 in accordance with one embodiment of the present invention is a general-purpose computer or processor capable of responding to and executing instructions in a defined manner. Other examples include a special-purpose computer including, for example, a personal computer (PC), a workstation, a server, a laptop computer, a web-enabled telephone, a web-enabled personal digital assistant (PDA), a microprocessor, an integrated circuit, an application-specific integrated circuit, a microprocessor, a microcontroller, a network server, a Java™ virtual machine, a logic array, a programmable logic array, a micro-computer, a mini-computer, or a large frame computer, or any other component, machine, tool, equipment, or some combination thereof capable of responding to and executing instructions.

In one non-limiting embodiment, system 100 is implemented as a PC. Furthermore, the system 100 may include a central processing engine including a baseline processor, memory, and communications capabilities. The system 100 also may include a communications system bus to enable multiple processors to communicate with each other. In addition, the system 100 may include storage 106 in the form of computer readable medium/media, such as a disk drive, disk, optical drive, a solid state drive, a tape drive, flash memory (e.g., a non-volatile computer storage chip), cartridge drive, and control elements for loading new software. In embodiments of the invention, one or more reference values may be stored in a memory associated with the device 102. Data, such as images produced by the methods and systems described herein may be organized on computer readable media in a database, which is an organized collection of data for one or more purposes, usually in digital form. In one embodiment, any or all software, data, code, processes, controllers, algorithms, instructions, etc. are stored non-transiently on a computer-readable medium.

Embodiments of the controller 104 may include, for example, a program, code, a set of instructions, or some combination thereof, executable by the device 102 for independently or collectively instructing the device 102 to interact and operate as programmed, referred to herein as "programming instructions". One example of a controller 104 is a software application (for example, operating system, browser application, client application, server application, proxy application, on-line service provider application, and/or private network application) installed on the device 102 for directing execution of instructions. In one embodiment, the controller 104 may be a Windows™ based operating system. The controller 104 may be implemented by utilizing any suitable computer language (e.g., C\C++, UNIX SHELL SCRIPT, PERL, JAVA™, JAVASCRIPT, HTML/DHTML/XML, FLASH, WINDOWS NT, UNIX/LINUX, APACHE, RDBMS including ORACLE, INFORMIX, and MySQL) and/or object-oriented techniques.

In one embodiment, the controller 104 may be embodied permanently or temporarily in any type of machine, component, physical or virtual equipment, storage medium, or propagated signal capable of delivering instructions to the device 102. In particular, the controller 104 (e.g., software application, and/or computer program) may be stored on any suitable computer readable media (e.g., disk, device, or propagated signal), readable by the device 102, such that if the device 102 reads the storage medium, the functions described herein are performed. For example, in one embodiment, the controller 104 may be embodied in various computer-readable media for performing the functions associated with processes embodying the methods described herein.

In one embodiment, the software is written and developed using a programming language, such as the C++ computing language. An integrated development environment (IDE), such as "DevC++, may be used to write the code. A person of ordinary skill in the art of computer programming and engineering will be able to develop and implement software capable of carrying out the tasks/operations described herein.

In use, the decellularized tissue described herein is orthotopically implanted into a patient, such as a human patient. As an example, in the case of a patient with a damaged or otherwise insufficient trachea, decellularized trachea tissue of an appropriate diameter that has been decellularized by a method described herein in which pressure is changed, is anastomosed to existing trachea in the patient.

Example 1

Decellularized Tracheal Extracellular Matrix Supports Epithelial Migration, Differentiation and Function We tested the hypothesis that decellularized tracheal scaffolds promote cellular invasion/repopulation and functional epithelialization in transplanted tracheal grafts. Employing unique orthotopic murine and rat tracheal transplant models we report the first evidence that decellularized tracheal scaffolds promote rapid functional cellular restoration and provide a rationale for continued development of this technology.

Materials and Methods

Animals. A total of 60 female C57BL/6 mice (approximately 12 weeks, and 20 g) were used in the study, half as donors and half as recipients.

Orthotopic tracheal transplantation. Recipient and donor animals were anesthetized with intraperitoneal injections of ketamine (80 mg/kg) xylazine (8 mg/kg). Animals were positioned in a supine position and maintained on a heating pad throughout the surgery. The tracheal reconstruction was performed with microscopic assistance as described previously (Hua, X., et al., Heterotopic and orthotopic tracheal transplantation in mice used as models to study the development of obliterative airway disease. J Vis Exp, 2010(35); Genden, E. M., et al., Orthotopic tracheal transplantation in the murine model. Transplantation, 2002. 73(9): p. 1420-5; Genden, E. M., et al., The kinetics and pattern of tracheal allograft re-epithelialization. Am J Respir Cell Mol Biol, 2003. 28(6): p. 673-81; and Genden, E. M., et al., Orthotopic tracheal allografts undergo reepithelialization with recipient-derived epithelium. Arch Otolaryngol Head Neck Surg, 2003. 129(1): p. 118-23). The ventral cervical trachea was exposed through a midline incision. The graft was then prepared by removing any loose connective tissue from the surface and liquid from the lumen, and was cut to a length of five cartilaginous rings. Care was taken to maintain the proximal-distal orientation of the grafts, particularly for the fresh transplants. A segment of three recipient tracheal rings was dissected from the surrounding connective starting approximately four rings below the larynx, with care not to damage the recurrent laryngeal nerves. Once the tracheal segment was freed, a transverse cut was made in the intracartilaginous tissue until a complete transection was performed. A second transection was performed to remove two complete rings of the trachea. Hemostasis was performed through the process. The distal anastomosis was performed first followed by the proximal anastomosis. In both cases, the anastomosis was performed with two interrupted 10-0 Prolene sutures placed near the dorsal ends of the cartilage rings and one or two sutures placed on the ventral aspect of the tracheal repair. The strap muscles were re-approximated, and the skin incision was the closed with interrupted 7-0 PDS sutures. Animals were allowed to recover from anesthesia. The operative time averaged 20 minutes. Among the donor tracheas, half were harvested and immediately implanted into a recipient. The other half were decellularized as described below. Among the recipients, a segment of the native tracheal was excised. The recipients were separated into two groups, and the trachea was reconstructed with either a fresh transplant or a decellularized trachea. Donor tracheas were placed in sterile physiologic saline on ice until transported to the lab for decellularization or until used for surgery (within approximately 20 minutes when used for surgery).

Post-operative care. After surgery, mice were housed in groups of four to five in standard cages, and food and water was supplied ad librum. The following medications were administered as subcutaneous injections for five days following surgery: buprenorphine (0.1 mg/kg) twice daily for pain relief, gentamicin (8 mg/kg) once daily for infection prophylaxis. At one, four, and eight weeks following surgery animals were sacrificed with intraperitoneal injections of ketamine/xylazine followed by immediate exsanguination, and the tracheas were harvested for analysis.

Decellularization. Tracheas were trimmed of extra tissue under a dissecting microscope (Zeiss StemiDV4) and were then frozen at −80° C. until time for surgery. The tracheas were thawed in deionized water at room temperature. Tracheas were then decellularized with fourteen 90-minute cycles each consisting of deionized water, then 3% Triton X-100, and then 3M NaCl treatments, leaving a decellularized tracheal scaffold. During this process, tracheas were subjected to cyclical pressure changes between room atmosphere and vacuum in a custom apparatus. For this experiment, the chamber was evacuated from ~0.1 MPa to 0.02 MPa in 20 seconds, held for 20 seconds, and then was pressurized from 0.02 MPa to ~0.1 MPa in 20 seconds. Finally, the decellularized scaffolds were agitated at 200 RPM on a shaker in a 0.1% peracetic acid (PAA)/4% ethanol solution for 90 minutes at 4° C. followed by three 30 minutes rinses in phosphate buffered saline (PBS), shaken at 200 RPM at 4° C. Scaffolds were then individually packaged in physiologic saline, and terminally sterilized by exposure to 20 kGy gamma irradiation.

Histology. Explants selected for histology were embedded in wax and deparaffinized in two xylene washes, followed by rehydration in an ethanol series. Antigen retrieval was performed using 10 mM citrate buffer in double distilled water. 5% bovine serum albumin in PBS was used as a blocking reagent. For the keratin-5 (K5)/keratin-14 (K14) dual stains, the following primary antibodies were applied: mouse anti-K14 (1:500 in blocking reagent) (Thermo/Neomarkers MS-115-P0) and rabbit anti-K5 (1:1000) (Covance PRB-160P). These primary antibodies were detected with appropriate secondary antibodies: AlexaFluor 488-conjugated goat anti-mouse $IgG_3$ (1:500) (Invitrogen A21151), AlexaFluor 594-conjugated donkey anti-rabbit (1:500) (Invitrogen A21207) Likewise, for acetylated tubulin (ACT)/Clara cell secretory protein (CCSP) dual stains, the following antibodies were applied: mouse anti-ACT $IgG_{2b}$ (diluted 1:20000) (Sigma T6793) and goat anti-CCSP (1:1000) (kindly provided by Dr. Peter Di, University of Pittsburgh). These were detected with: donkey anti-mouse IgG (H+L) 594 (1:500) (Jackson Immuno 715-485-150), and donkey anti-goat IgG (H+L) 488 (1:500) (Jackson Immuno 715-515-150). All slides were counterstained with VectaShield Mounting Medium with DAPI (Vector Laboratories H-1200). Completed slides were examined with an Olympus IX71 florescence microscope (Nikon) and the images were captured with Nikon cellSens Dimension (version 1.5). Adobe Photoshop CS5 was used to form a mosaic of all the images from a given slide for quantification.

Quantification. ImageJ (NIH, Bethesda, Md.) was used to measure the length of several basement membrane segments along each explanted tracheal lumen. For each measured segment, DAPI-stained and antibody-immunolabeled cells along the segment were hand-counted in order to determine cell densities (cells/μm). Mean cell densities were calculated for each explanted trachea at each timepoint.

Cilia beat frequency evaluation. Three tracheas from each treatment group were harvested eight weeks after surgery. Strips of tracheal tissue were secured luminal side down on a 35-mm glass-bottomed culture dish (Willco Wells) using a glass coverslip covered with a silicone sheet containing a small window to form a chamber. Cilia dynamics were captured along the edge of the trachea strips at room temperature with a ×100 differential interference contrast (DIC) oil objective and a Leica inverted microscope (Leica DMIRE2), and movies [200 frames/s (fps)] were made with a Phantom v4.2 camera (Vision Research). To quantify ciliary beat frequency (CBF), ImageJ was used to examine cyclic variations in pixel intensities corresponding to ciliary strokes. More than three randomly selected areas were imaged from each of trachea in order to calculate mean native and graft CBF for each treatment group.

Micro computed tomography. Three-dimensional image acquisition of explanted tracheas was carried out using a high resolution micro-CT (Siemens, Inveon Multimodality, Munich, Germany) at 12 µm image resolution at 80 kVe and 500 µm X-ray. 3D surface volume rendering image was reconstructed using OsiriX software.

Statistics. Statistical analysis was performed using Graph-Pad Prism 6 (GraphPad, La Jolla, Calif.). Data are presented as mean±one standard deviation (SD) for each group. For weight change and survival analysis, linear regression and log-rank (Mantel-Cox) tests were performed, respectively. Differences in cell counts and ciliary beat frequencies between untreated controls, fresh transplants, and decellularized transplants were assessed with two-way analysis of variance (ANOVA) with Tukey's multiple comparisons test. Statistical significance was defined as p-value <0.05.

Results

Figure 1B:
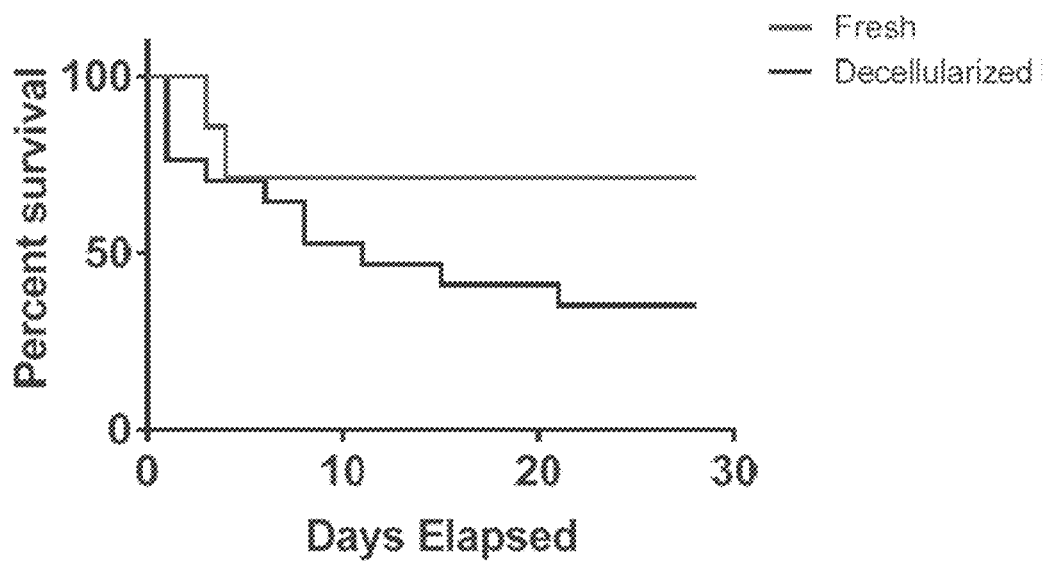
Figure 1C:
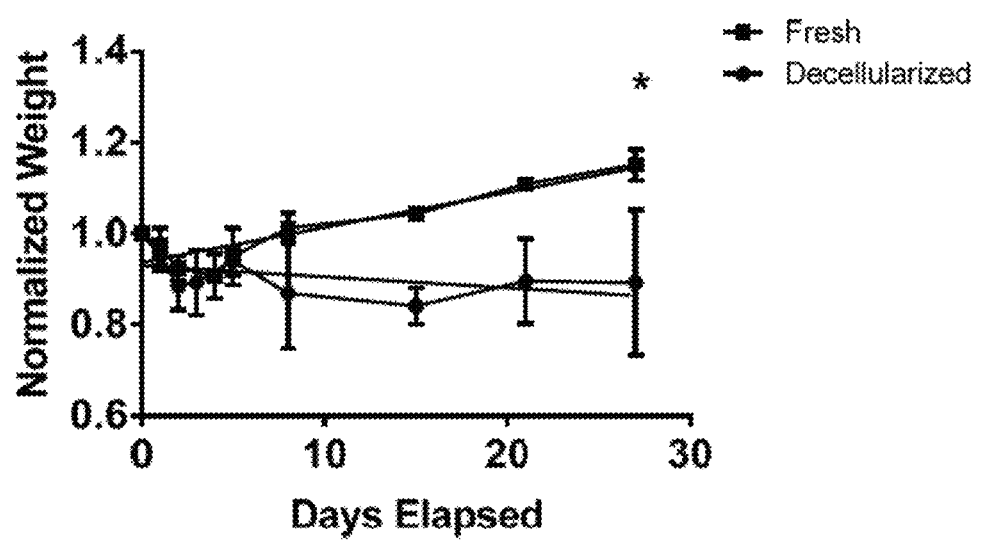

Orthotopic tracheal transplantation rescues mice following tracheal loss. Tracheal loss is often fatal, whereas lack of pre-clinical models has hindered tracheal replacement development (Grillo, H. C., Tracheal replacement: a critical review. *Ann Thorac Surg*, 2002. 73(6): p. 1995-2004). We tested the hypothesis that orthotopic decellularized tracheal transplant would rescue mice following full thickness tracheal loss. We performed orthotopic transplantation using fresh and decellularized grafts in age matched female mice as described. Representative images show excellent healing of the fresh tracheal transplant rescuing mice from full thickness tracheal loss (FIG. 1B, 1C). In early studies, the survival rate for mice receiving fresh transplants was 71.4% (n=7) (FIG. 1B). Mean weight gain for surviving animals was 15.1±3.4% over the 28-day period following surgery (FIG. 1C).

Orthotopic transplantation of decellularized tracheal scaffolds rescues mice from full thickness tracheal loss. Though freshly harvested tracheal grafts successfully salvaged mice after acute tracheal loss, it was not clear if similar results would be obtained using decellularized tracheal scaffold. We decellularized adult murine tracheas achieving complete cellular removal. We rescued 35.3% (n=17) of mice from full tracheal loss with decellularized tracheal transplants (FIG. 1B). Surviving animals lost weight over the 28-day study period, dropping to 89.2±16.0% of their starting weight.

Figures 1, 2:
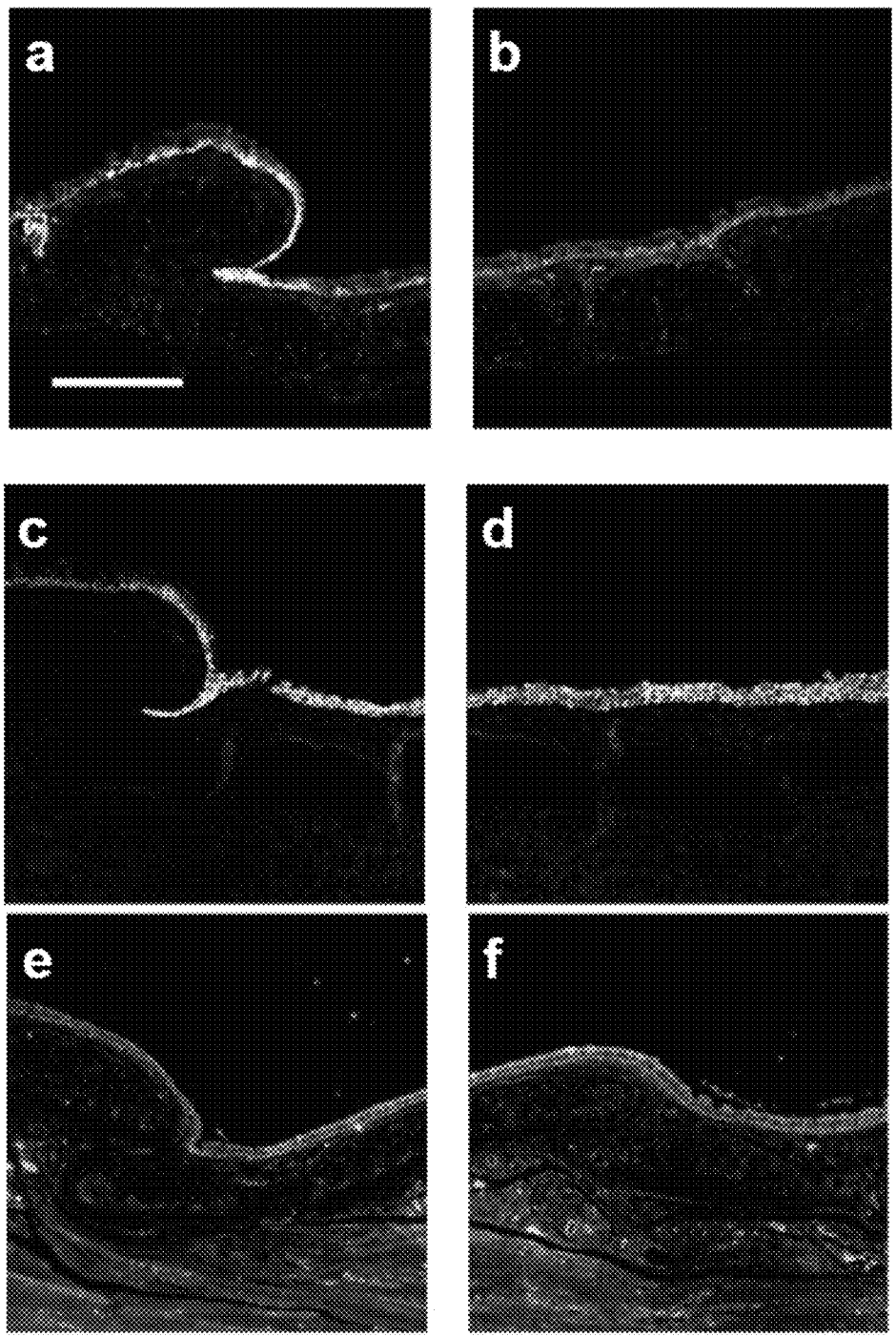
FIG. 2-1 through 2-3. Histologic quantification of basal cell protein expression in mouse trachea transplants. Mice receiving fresh (a, b, e, f, i, j) or decellularized (c, d, g, h, k, l) transplants were sacrificed one (a-d), four (e-i), or eight (i-l) weeks following surgery and immunofluorescent labeling for basal cell markers was performed. Images are shown at a site of anastomosis (a, e, i, c, g, k) or at a mid-graft region (b, f, j, d, h l). Cells expressing keratin-5 (K5, red, m), keratin-14 (K14, green, n), and dual-expressing (yellow, o) cells along the basement membrane were counted in order to determine cell densities (cells/μm). Columns labeled "Ctrl" denote cell densities for untreated, native trachea from C57BL/6 mice. Scale bar 200 μm.
Figure 2:
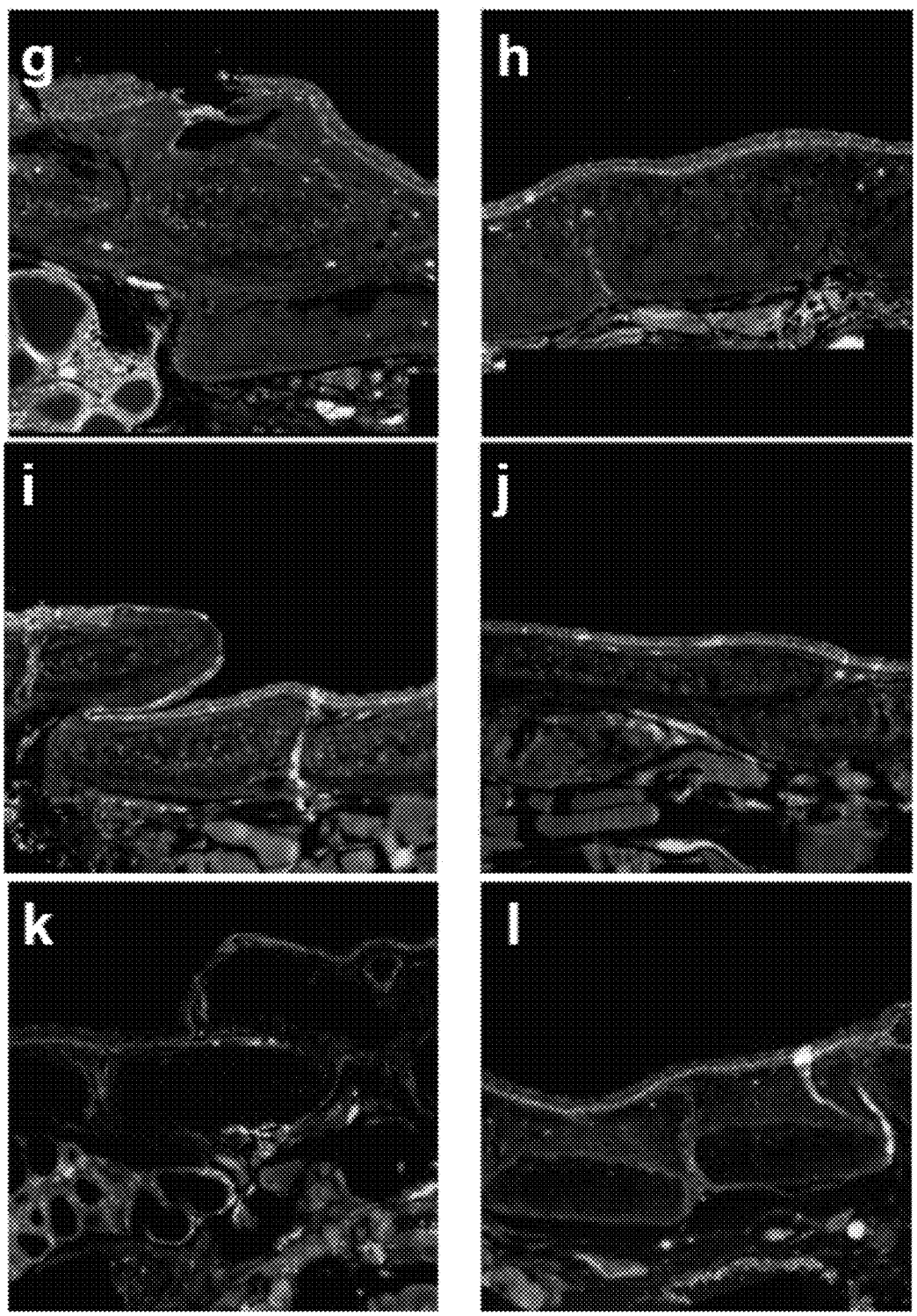
Figures 1, 3:
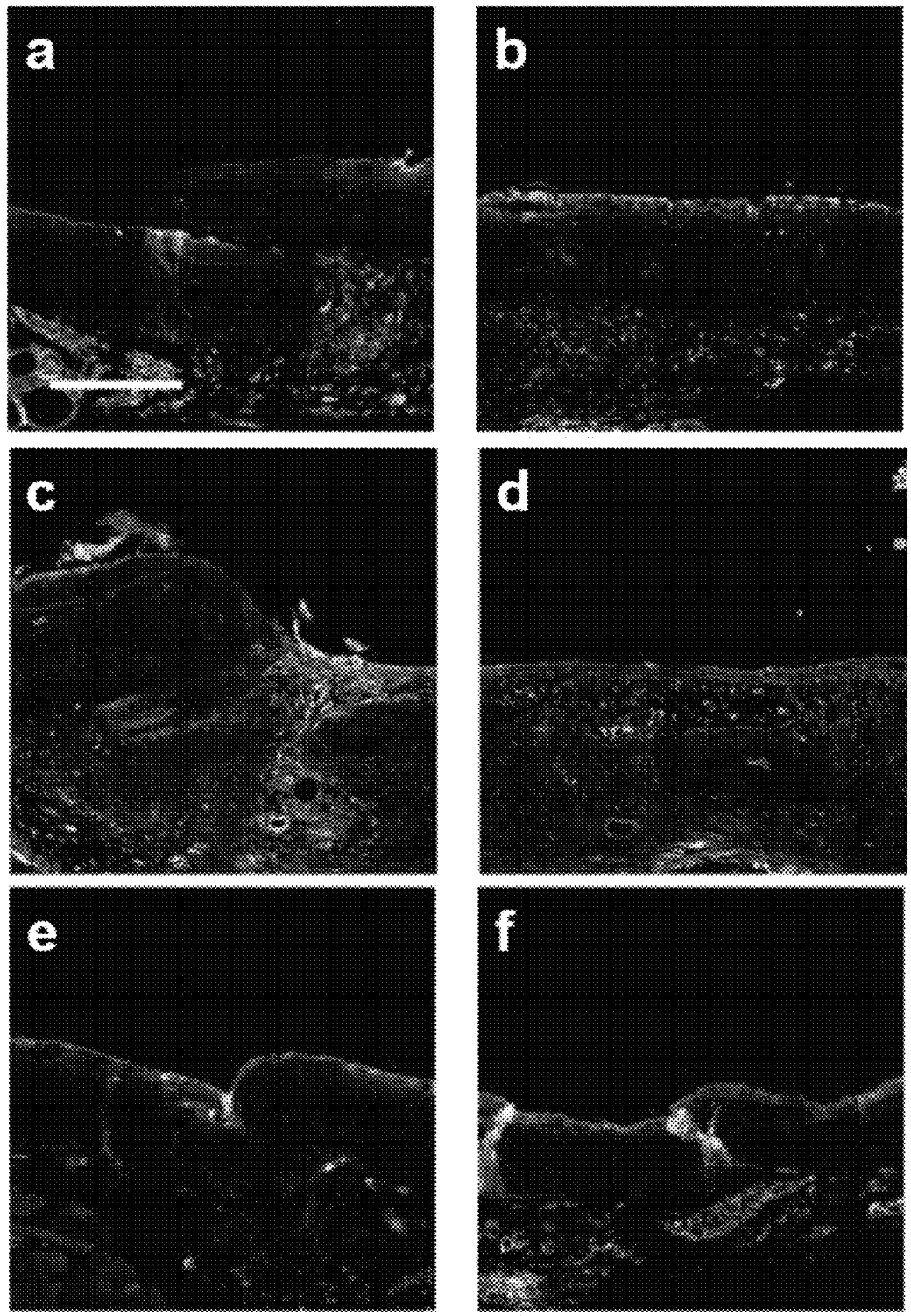
Figures 2, 3:
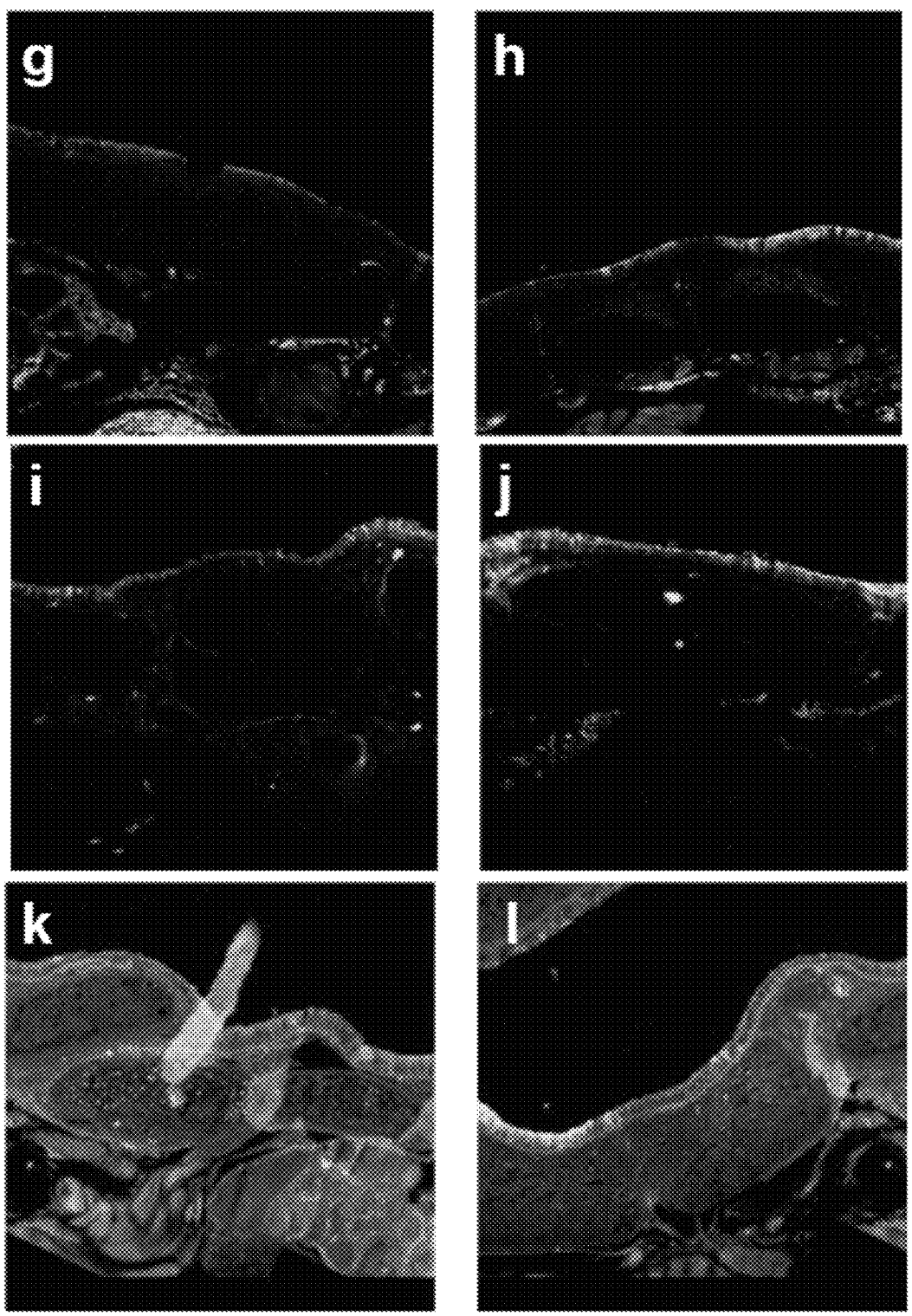
Figure 3:
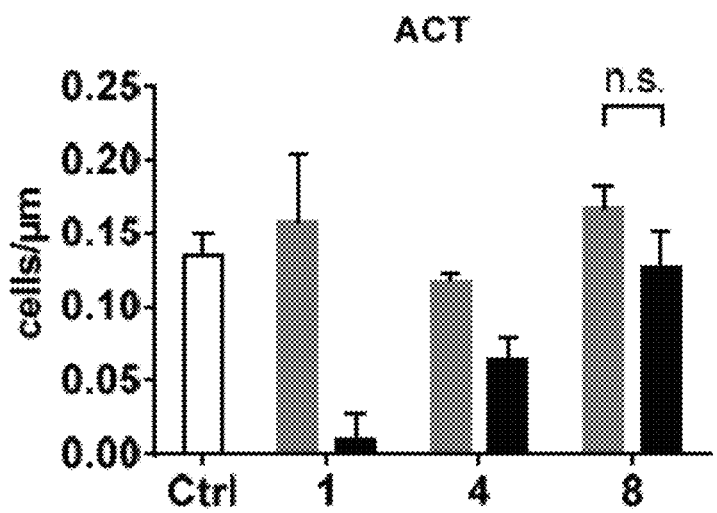
Figure 3:
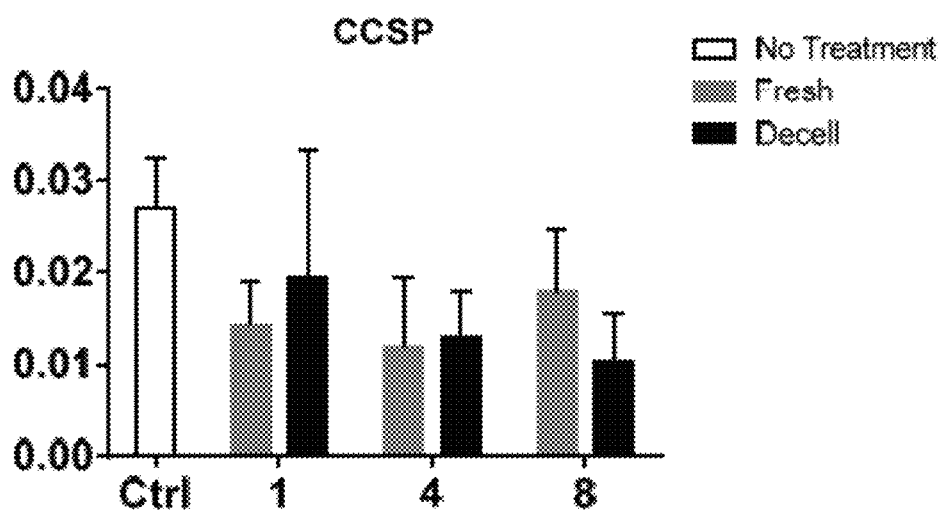

Decellularized tracheal scaffolds display epithelial restoration following orthotopic transplantation. Our finding that decellularized tracheal scaffolds rescued mice from full thickness tracheal defects suggested that the decellularized scaffolds reconstituted the cellular population. Immunofluorescent labeling of fresh and decellularized grafts post-transplant demonstrated complete resurfacing of the internal surface of transplanted decellularized grafts (FIGS. 2-1 through 2-3, and 3-1 through 3-3). Time course quantification of cell specific repopulation of the tracheal scaffold was performed. Though resurfacing of the decellularized tracheal scaffold lumen was complete within eight weeks (FIGS. 2-1 through 2-3, and 3-1 through 3-3), there were cell type specific variations. Within the first week following surgery, we observed rapid repopulation of the luminal surface with a large number of keratin-5/keratin-14 dual-expressing (K5+/K14+) cells and a small number of keratin-5 negative/keratin-14 positive (K5-/K14+) cells (FIGS. 2-1 and 2-2, d, h, i). Over successive time-points the population of K5+/K14+ cells steadily declined while the proportion of K5+/K14- and ACT+ cells increased (FIG. 2-3, m-o, and FIG. 3-3, m). This same pattern was observed at the interface between native and graft tissue in fresh transplants (FIGS. 2-1 and 2-2, a, e, i). At eight weeks post-transplant the regenerated epithelium contained similar numbers of K5+/K14+, K5-/K14+, and K5+/K14+ cells compared to fresh orthotopic tracheal transplants (FIG. 2-3, m-o). Total numbers of secretory cells per micrometer though initially not significantly different from numbers in fresh transplants were decreased in decellularized grafts after eight weeks (FIG. 3-3, n). Cartilaginous portions of the decellularized trachea did not repopulate over the course of the study period.

Figure 4A:
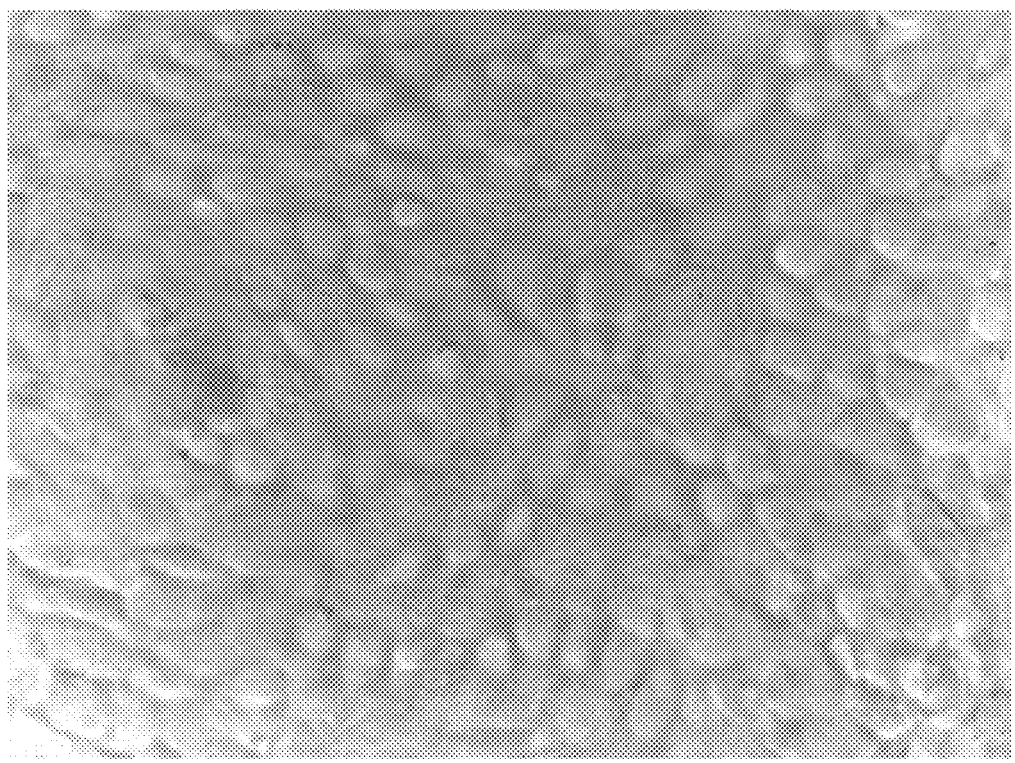
FIGS. 4A and 4B. Ciliated cell function of orthotopic fresh and decellularized tracheal transplants. Real time video microscopy was employed to quantify ciliary activity eight weeks after transplantation. Image from decellularized graft shown in FIG. 4A; calculated ciliary beat frequencies shown in FIG. 4B. Column labeled "Ctrl" denotes ciliary beat frequency for untreated, native trachea from C57BL/6 mice.
Figure 4B:
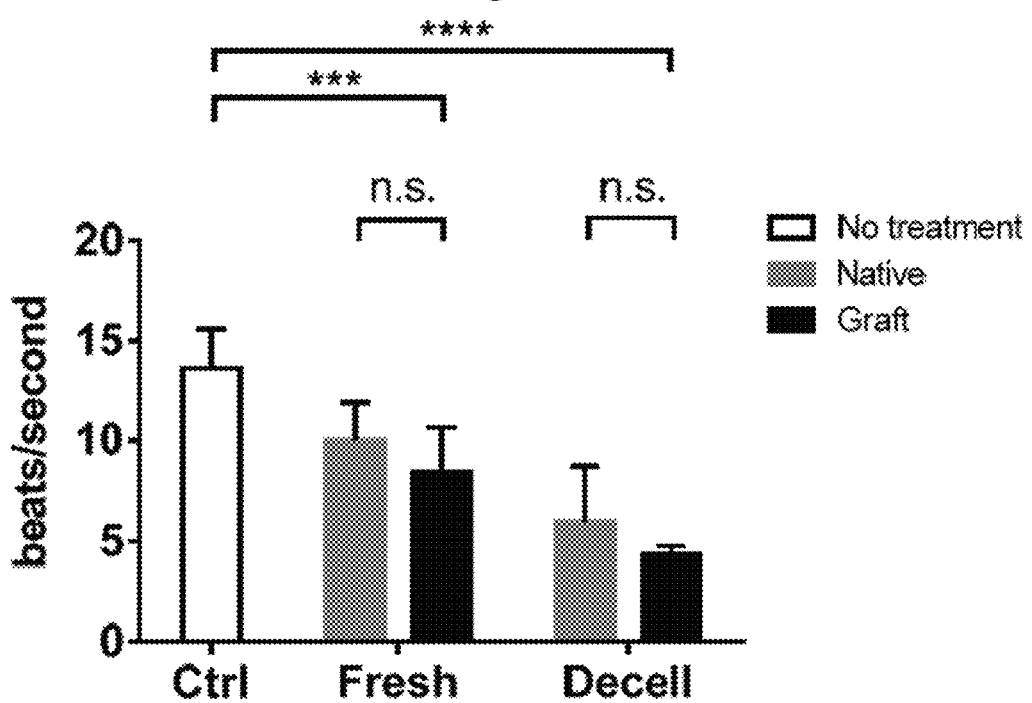

Cilia function is diminished in decellularized tracheal transplants. A critical feature of the healthy trachea is the ability to handle secretory load (REF), and a robust ciliated cell response is a minimal requirement for engineered tracheal transplants. We used state-of-the-art real-time microscopic imaging to assess cilia function in our decellularized and fresh tracheal transplants (a movie was captured showing restoration of cilia function within decellularized tracheas. Videos were captured at 200 frames/second, and exported at 30 frames/second) and calculate ciliary beat frequency (CBF). We observed the presence of functional cilia in both decellularized and fresh orthotopic tracheal grafts. In both fresh and decellularized transplant groups, CBF for cells along the graft was not significantly different than adjacent native tissue. However, ciliary beat frequency in both fresh and decellularized grafts was significantly lower than that of native, untreated trachea (FIG. 4B).

Figure 5:
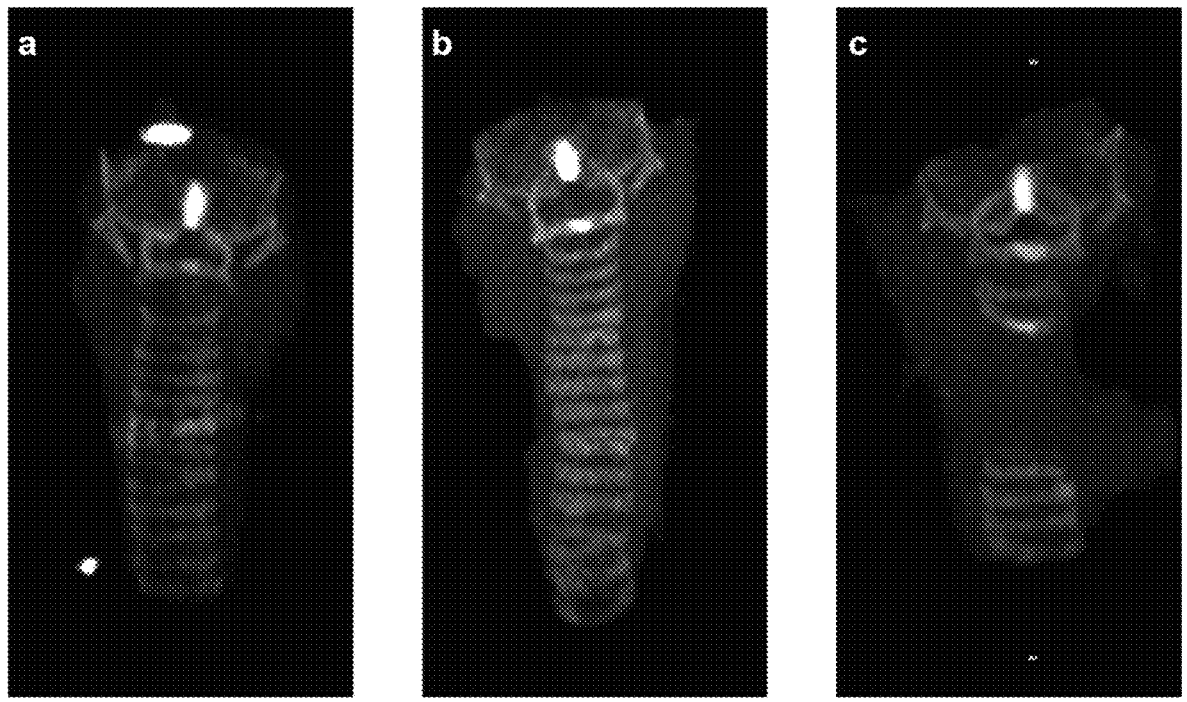
FIG. 5. Micro-computed tomography analysis of fresh orthotopic tracheal transplants. Representative images shown from computed tomography performed on explanted trachea from wild type, untreated C57BL/6 mice (a), mice receiving fresh transplants (b), and mice receiving decellularized transplant (c).

Tracheal diameter is maintained in orthotopic tracheal transplants. The current generation of engineered tracheal transplants has been complicated by loss of structural integrity and an inability to maintain tracheal diameter (Kocyildirim, E., et al., Long-segment tracheal stenosis: slide tracheoplasty and a multidisciplinary approach improve outcomes and reduce costs. *J Thorac Cardiovasc Surg*, 2004. 128(6): p. 876-82). We assessed tracheal morphology using micro-computed tomography (FIG. 5). Cartilaginous rings were visible as radiopaque structures in fresh transplants (FIG. 5b), as they were in wild-type untreated controls (FIG. 5a), but could not be visualized in decellularized transplants (FIG. 5c).

Discussion

This example provides quantification and functional assessment of the first ever murine model of orthotopic, decellularized tracheal transplant. Long term survival was achieved in a significant majority of cases (>70%) of fresh tracheal transplants and in a minority of cases in decellularized tracheal transplants; this difference trended toward significance at p=0.169. Transplant failures occurred from anastomosis separation between the normal tracheal remnant and the transplant, and emphasize the need for care in placing and securing the back and front wall sutures.

The trachea is potentially an ideal candidate for repair using a decellularized graft. A mature epithelium is a desirable component of any tracheal graft, in order to (1) act as a barrier defense and (2) to provide mucociliary clearance. It has been reported that a confluent epithelial layer can reduce or even prevent fibrosis and ultimate stenosis of a tracheal graft (Okumura, N., et al., Experimental study on a new tracheal prosthesis made from collagen-conjugated mesh. *J Thorac Cardiovasc Surg*, 1994. 108(2): p. 337-45 and Teramachi, M., et al., Intrathoracic tracheal reconstruction with a collagen-conjugated prosthesis: evaluation of the efficacy of omental wrapping. *J Thorac Cardiovasc Surg*, 1997. 113(4): p. 701-11). We observed complete resurfacing of the decellularized tracheal lumen by the end of the first week, following early proliferation of K5+/K14+ cells. The tracheal lining is complex, and composed of heterogeneous cell populations, some of which act as progenitor cells (Musah, S., et al., Repair of tracheal epithelium by basal cells after chlorine-induced injury. *Respir Res*, 2012. 13: p. 107 and Cole, B. B., et al., Tracheal Basal cells: a facultative progenitor cell pool. *Am J Pathol*, 2010. 177(1): p. 362-76). Previous studies have demonstrated that K5+/K14+ cells represent a precursor cell population with the capacity to develop into ciliated (ACT+) and secretory (CCSP+) cells (Cole, B. B., et al., 2010. 177(1): p. 362-76). This finding is supported by our histological data, which shows a correlation between the depletion of the K5+/K14+ cell population and the generation of a mature differentiated epithelium (FIGS. 2-1 through 2-3, and 3-1 through 3-3). Similarly, in animals receiving fresh transplants, the presence of K5+/K14+ cells near sites of anastomosis suggests that this cell population plays a role in epithelial healing (FIG. 2-1, a). Real-time microscopy demonstrates the presence of a functional ciliated epithelium eight weeks following surgery in both fresh and decellularized transplant groups (FIG. 4A).

Figure 6:
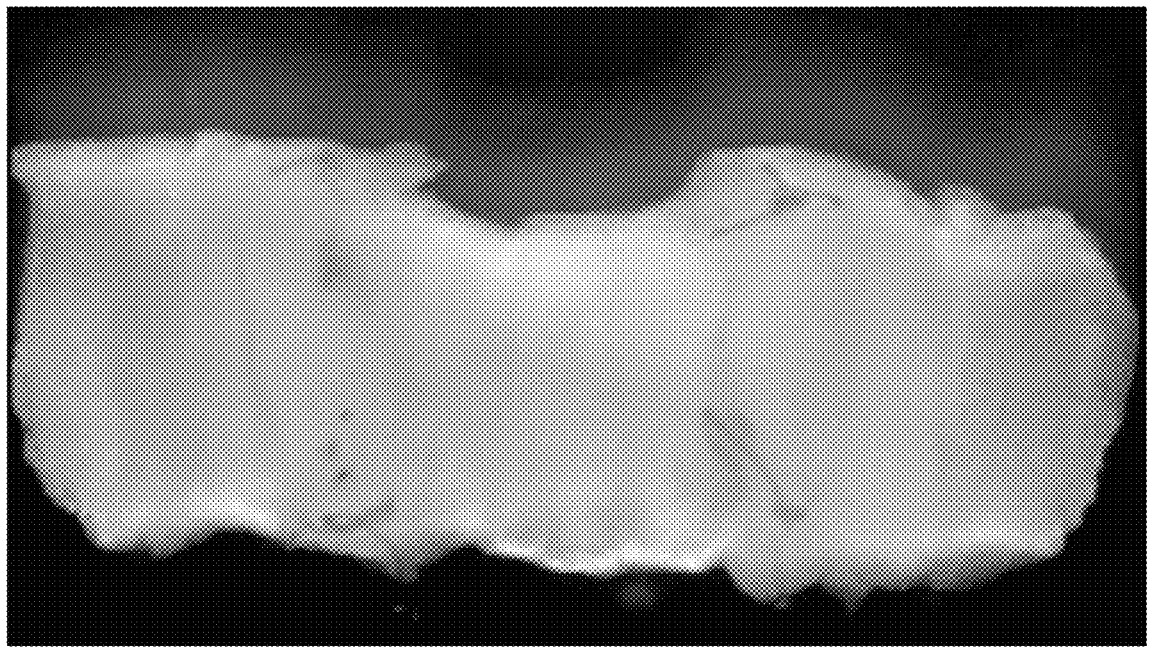
FIG. 6. Decellularized tracheas maintain patency after eight weeks.

Histologically, we observed that cartilaginous portions of the decellularized trachea remain acellular throughout the course of the healing period, while chondrocytes within the fresh tracheal transplants are maintained. Computed tomography (FIG. 5) demonstrated radiolucent cartilaginous rings within decellularized grafts after eight weeks. Scans performed on decellularized grafts before transplantation similarly demonstrated a lack of visible radiopaque cartilage (data not shown). These findings suggest that cartilaginous rings lose their molecular structure during the process of decellularization, and are not repopulated after transplantation. Despite the presumptive loss of mechanical structure associated with the degradation of the cartilaginous rings, decellularized tracheal grafts maintained their patency over eight weeks (FIG. 6).

These data demonstrate this model to be a reliable preclinical platform for research and capture the high-throughput aspect of mice while harnessing the power of mutant murine models to test fundamental questions wound healing from a molecular perspective.

Example 2

Additional Tissues

In addition to trachea, airway (trachea and vocal fold); esophagus; liver; small or large intestine; dermis; cardiovascular (myocardium, heart valve, and both thoracic and abdominal aorta); and ocular (retina) tissue have been similarly successfully processed. CNS (optic nerve, brain, spinal cord, peripheral nerve, dura mater); peripheral vasculature; orthopaedic (nucleus polposus, cartilage (TMJ, knee meniscus), tendon, bone); skeletal muscle; pancreas; and lung tissue are processed in a similar manner.

Example 3

Processing of Porcine Dermis and Porcine Aorta

Figure 11:
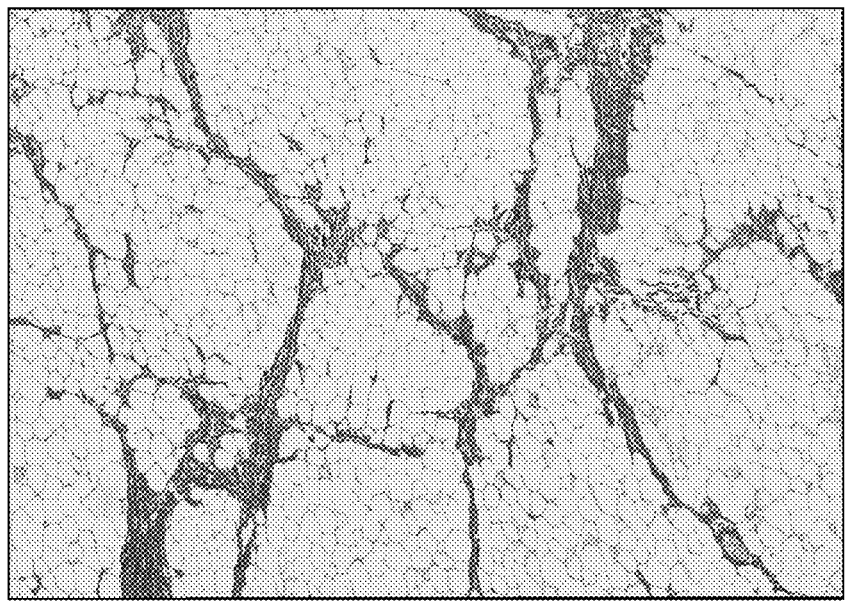
FIG. 11 Top: Decellularized dermis stained with hematoxylin and eosin, bottom native porcine dermis.
Figure 11:
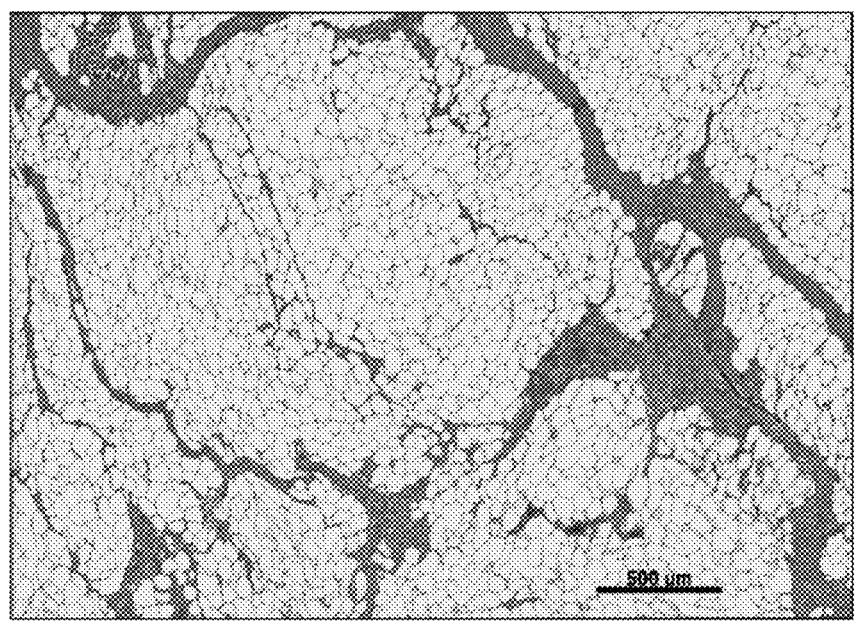

Porcine dermis and aorta were prepared according to the following protocol. The tissue was prepared in 14 steps over 14 days, each step comprising treatment of the tissue in four separate solutions (DI water, 3% triton X-100, 3M NaCl, and 2,000 KU DNAse I in 1M NaCl), each treatment comprising 30 one-minute cycles. The for each cycle, the chamber was evacuated from ~0.1 MPa to 0.006 MPa in 30 seconds, held at 0.006 MPa for 25 seconds, and then pressurized from 0.006 MPa to ~0.1 MPa in 5 seconds. Samples were rinsed at 200 RPM in a flask between days for 8 hours in PBS FIG. 11: Top: Decellularized dermis stained with hematoxylin and eosin, bottom native porcine dermis.

Figure 12:
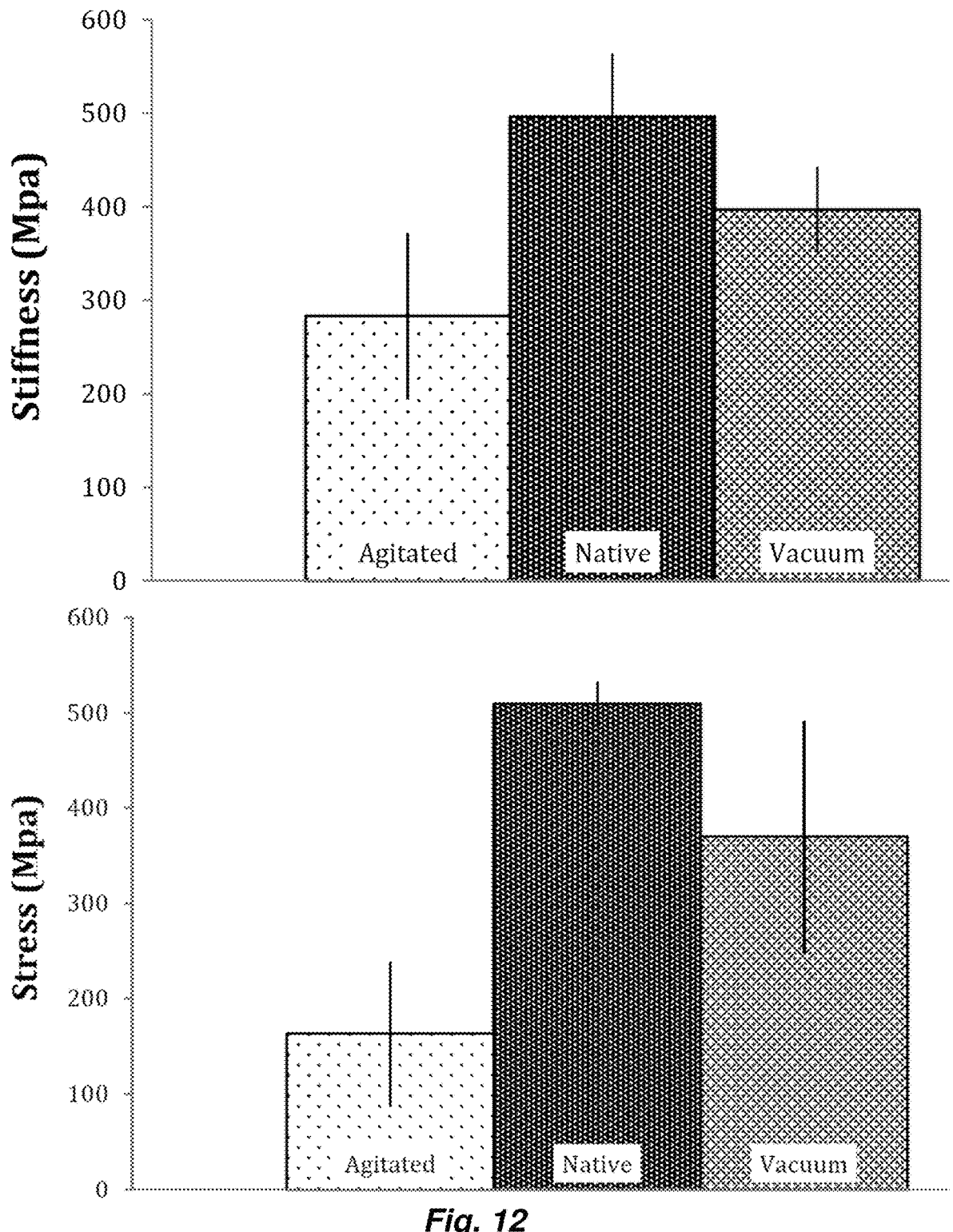
FIG. 12 Comparing mechanical properties of native, vacuum decellularized, and agitation decellularization control obtained from a scaled ASTM ball burst test. Top: Maximum stiffness calculated over a 20% moving window. Bottom. Stress at failure.

FIG. 12. Comparing mechanical properties of native, vacuum decellularized, and agitation decellularization control obtained from a scaled ASTM ball burst test. Top: Maximum stiffness calculated over a 20% moving window. Bottom. Stress at failure. FIG. 12 demonstrates increased retention of native mechanical properties during decellularization.

Figure 13:
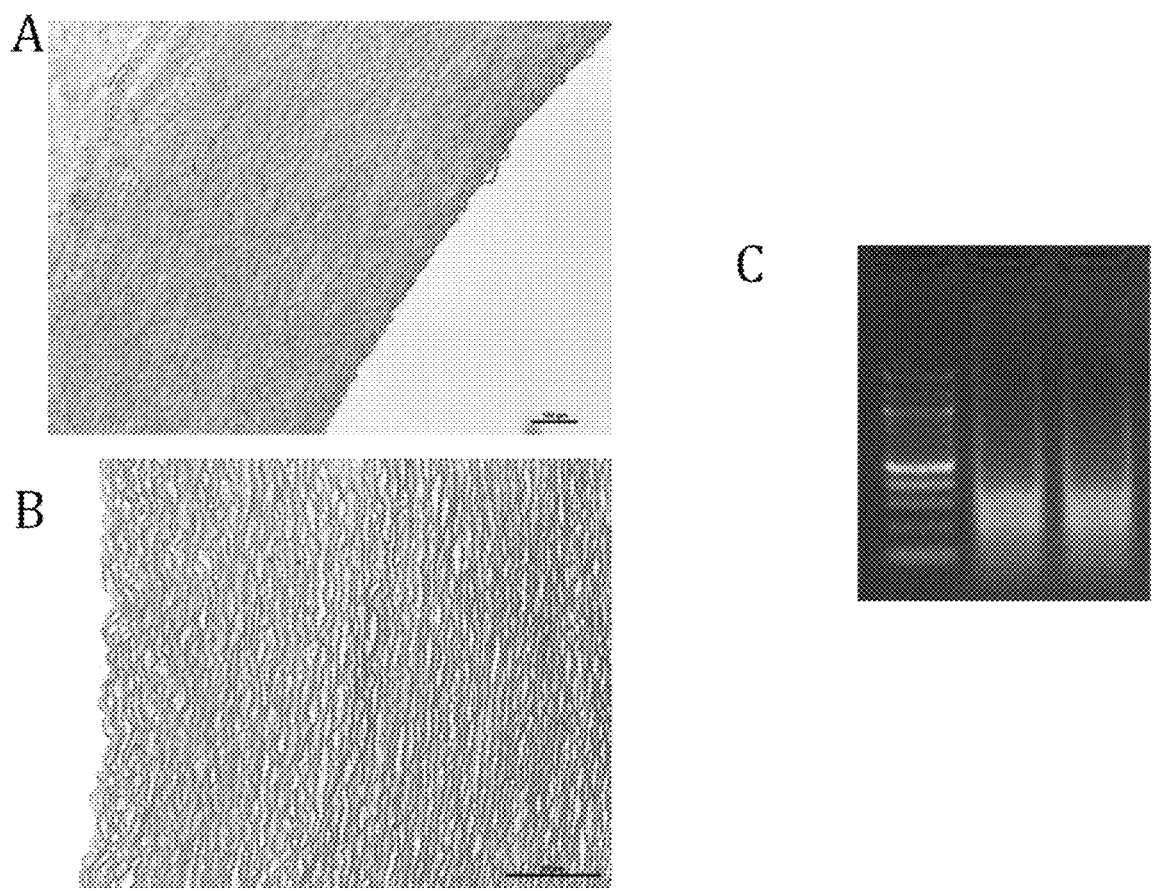
FIG. 13 A: Hematoxylin and eosin stain of native porcine aorta. B. Hematoxylin and eosin stain of decellularized porcine aorta. C. DNA gel electrophoresis of vacuum decellularized porcine aorta. First lane is a 100-1200 base pair DNA ladder. Right hand lanes demonstrate remnant DNA fragment lengths of vacuum decellularized aorta are reduced to less than 300 base pairs.

FIG. 13: A: Hematoxylin and eosin stain of native porcine aorta. B. Hematoxylin and eosin stain of decellularized porcine aorta. C. DNA gel electrophoresis of vacuum decellularized porcine aorta. First lane is a 100-1200 base pair DNA ladder. Right hand lanes demonstrate remnant DNA fragment lengths of vacuum decellularized aorta are reduced to less than 300 base pairs.

Figure 14:
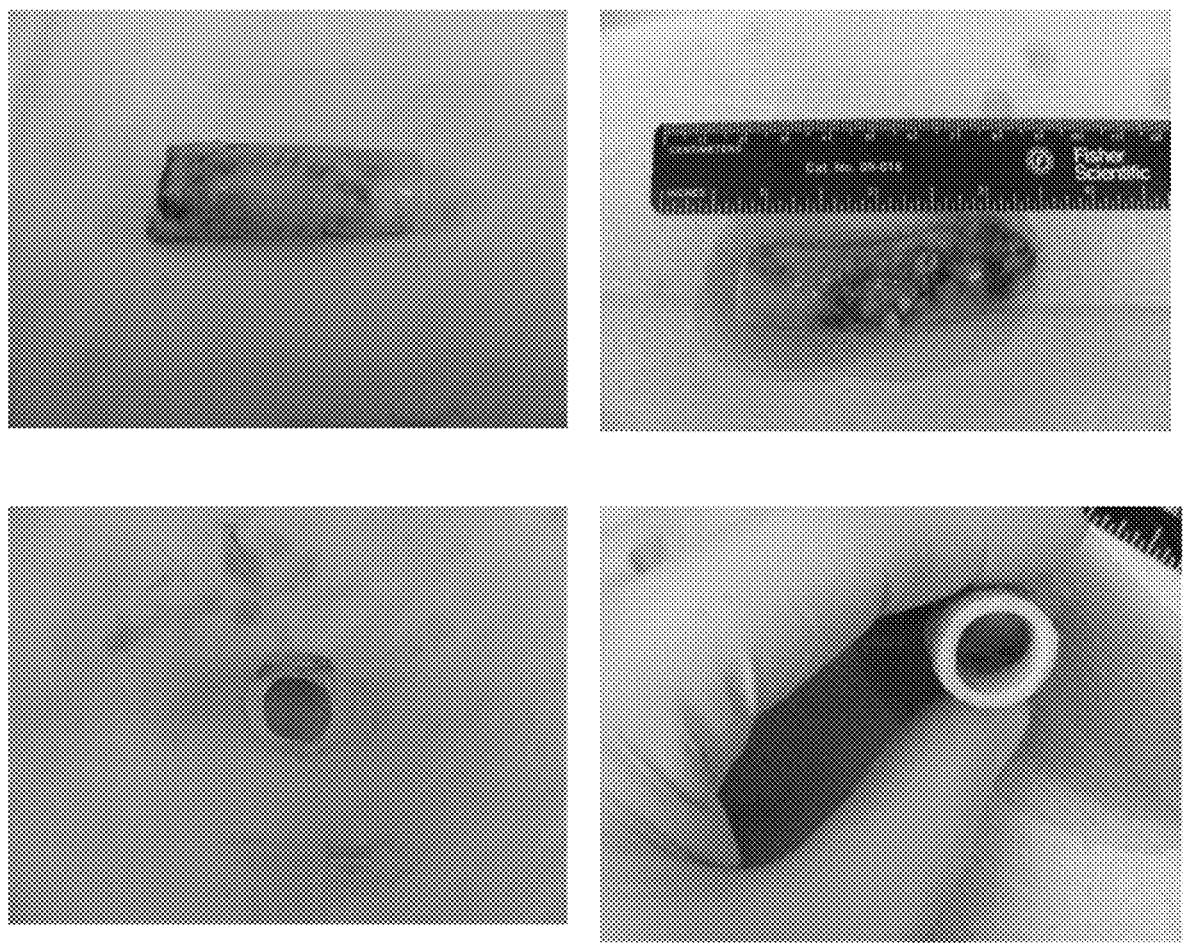
FIG. 14. 12 week explants of decellularized porcine aortas implanted in a 15 kg piglet partial circumference aortic reconstruction model.

FIG. 14. 12 week explants of decellularized porcine aortas implanted in a 15 kg piglet partial circumference aortic reconstruction model. Grafts are quickly incorporated into surrounding native tissue. Explants do not demonstrate dilation, stenosis, or necrosis.

Figure 8A:
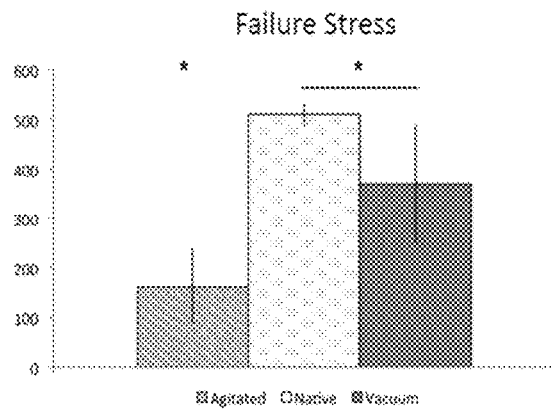
FIGS. 8A and 8B are graphs showing Failure Stress (FIG. 8A) and Maximum Stiffness (FIG. 8B) as described in Example 3.
Figure 8B:
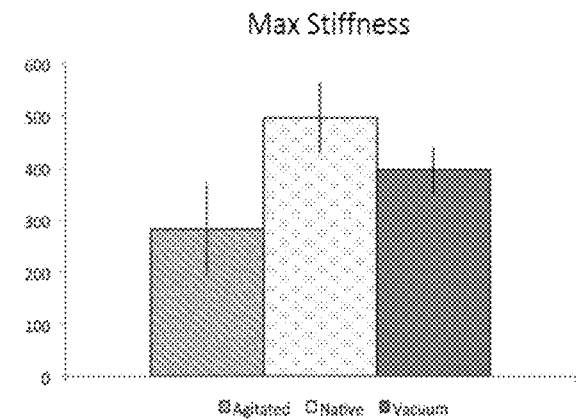

FIGS. 8A and 8B are graphs showing the superior mechanical properties, including Failure Stress (FIG. 8A) and Maximum Stiffness (FIG. 8B) indicating that ECM material prepared by vacuum decellularization according to the methods described herein achieves superior mechanical properties as compared to prior agitation-only processes, with the added benefit that strong agitation, which disrupts fragile tissues, is not needed.

Example 4

Porcine Vocal Fold

Figure 9:
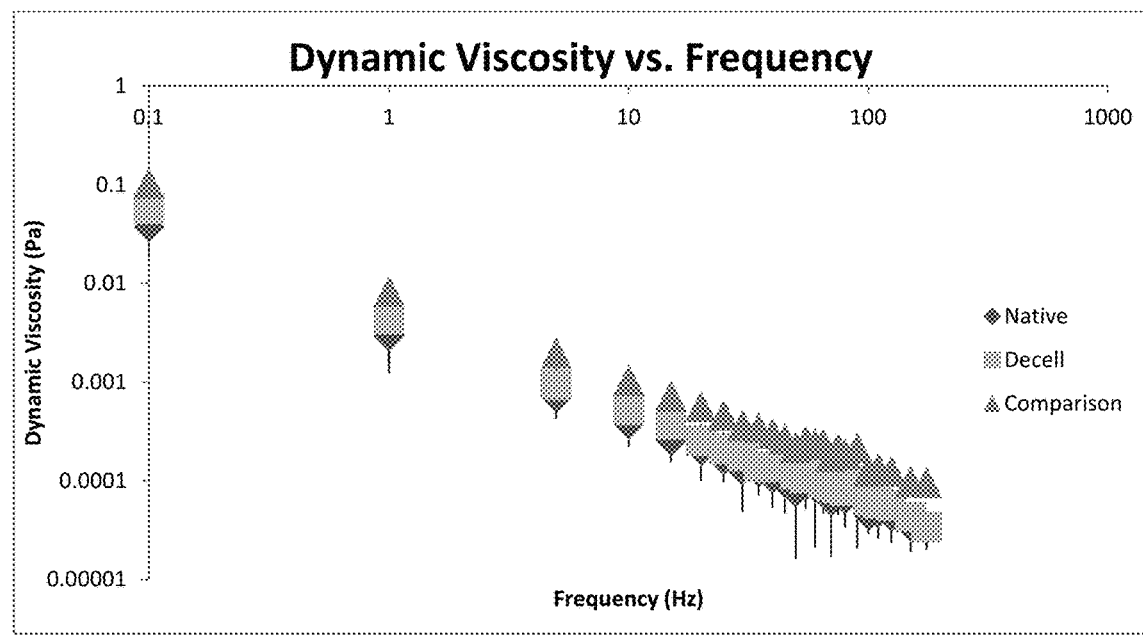
FIG. 9 is a graph showing Dynamic Viscosity versus Frequency, according to Example 4.

Porcine vocal fold tissue was prepared essentially as described above. FIG. 9 is a graph showing dynamic viscosity.

Example 5

Porcine Brain

Porcine vocal fold tissue was prepared essentially as described above, with 9 cycles each comprising 3 solutions (DI water, 3% Triton X-100, 3M NaCl) each comprising 30 one minute cycles: Cycle Pressure Ramp rate (evacuate chamber from ~0.1 MPa to 0.014 MPa in 30 seconds, depressurize 0.014 MPa to ~0.1 MPa in 30 seconds).

The present invention has been described in accordance with several examples, which are intended to be illustrative in all aspects rather than restrictive. Thus, the present invention is capable of many variations in detailed implementation, which may be derived from the description contained herein by a person of ordinary skill in the art.

The invention claimed is:
1. A system for decellularization of tissue, comprising:
a) an airtight chamber capable of withstanding varying pressures;
b) a decellularization solution comprising one or more enzymes selected from a protease and a DNase enclosed within the airtight chamber;

c) a vacuum pump connected to the airtight chamber capable of cyclically varying pressure in the airtight chamber over at least one cycle in the airtight chamber;

d) one or more valves for controlling air flow into and from the airtight chamber; and e) a computer control comprising one or more processors programmed or configured to control the vacuum pump and the one or more valves to change pressure within a range of −0.095 MPa to about 0.415 MPa over at least one cycle in the airtight chamber at a rate of 0.25 MPa/s to 0.0001 MPa/s.

2. The system of claim 1, in which the pressure change in the airtight chamber comprises a cycle length from 15 seconds to one hour, a pressure change of at least 25%, and at least 10 pressure changes.

3. The system of claim 1 wherein the decellularization solution further comprises a substance selected from the group consisting of a detergent, a surfactant, a sugar, a salt, and an acid, a protease, and a DNAse.

4. The system of claim 1 wherein the decellularization solution further comprises a substance selected from the group consisting of SDS, CHAPS, deoxycholate, Triton X-100, trypsin, proteinase K, glucose, urea, peracetic acid, and ethanol.

5. The system of claim 1 wherein the pressure is changed cyclically with a frequency of 5 seconds to 30 minutes.

6. The system of claim 1 further comprising an agitator.

7. The system of claim 1 wherein the tissue is selected from the group consisting of brain, vascular, cardiac tissue, small intestine, urinary bladder, liver, skin, vocal cord, esophagus, large intestine, aorta, ocular, optic nerve, spinal cord, peripheral nerve, dura mater, cartilage, tendon, bone, nucleus polposus, skeletal muscle, pancreas, lung, amnion, chorion, placenta, and trachea tissue.

8. The system of claim 1 wherein the rate of pressure change in the airtight chamber during pressurization or evacuation is about 0.003 MPa/s.

9. The system of claim 1 further comprising a lyophilizer.

* * * * *

UNITED STATES PATENT AND TRADEMARK OFFICE
CERTIFICATE OF CORRECTION

Page 1 of 1

PATENT NO. : 11,185,611 B2
APPLICATION NO. : 15/983150
DATED : November 30, 2021
INVENTOR(S) : Thomas W. Gilbert et al.

It is certified that error appears in the above-identified patent and that said Letters Patent is hereby corrected as shown below:

In the Claims

Column 17, Line 20, Claim 3, delete "acid, a protease, and a DNAse." and insert -- acid. --

Signed and Sealed this
Eighteenth Day of January, 2022

Drew Hirshfeld
*Performing the Functions and Duties of the*
*Under Secretary of Commerce for Intellectual Property and*
*Director of the United States Patent and Trademark Office*